US008802631B2

(12) United States Patent
Erlich et al.

(10) Patent No.: US 8,802,631 B2
(45) Date of Patent: Aug. 12, 2014

(54) PEPTIDES AND METHODS FOR THE TREATMENT OF GLIOMAS AND OTHER CANCERS

(75) Inventors: Rafael Bierig Erlich, Queensland (AU); Luciana Chiarini, Rio de Janeiro (BR); Vilma R. Martins, Sao Paulo (BR); Rafael Linden, Rio de Janeiro (BR); Vivaldo Moura Neto, Rio de Janeiro (BR)

(73) Assignee: Ludwig Institute for Cancer Research Ltd., New York, NY (US)

( * ) Notice: Subject to any disclaimer, the term of this patent is extended or adjusted under 35 U.S.C. 154(b) by 654 days.

(21) Appl. No.: 12/678,467

(22) PCT Filed: Sep. 17, 2008

(86) PCT No.: PCT/US2008/076699
§ 371 (c)(1),
(2), (4) Date: Mar. 16, 2010

(87) PCT Pub. No.: WO2009/039188
PCT Pub. Date: Mar. 26, 2009

(65) Prior Publication Data
US 2010/0209429 A1    Aug. 19, 2010

Related U.S. Application Data

(60) Provisional application No. 60/972,958, filed on Sep. 17, 2007.

(51) Int. Cl.
| | |
|---|---|
| *A01N 61/00* | (2006.01) |
| *A61K 31/00* | (2006.01) |
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *G01N 33/00* | (2006.01) |

(52) U.S. Cl.
USPC .............. 514/19.3; 514/1; 514/1.1; 514/19.2; 530/300; 530/324; 436/86

(58) Field of Classification Search
None
See application file for complete search history.

(56) References Cited

U.S. PATENT DOCUMENTS

2003/0138848 A1* 7/2003 Moarefi et al. ................ 435/7.1
2005/0196754 A1* 9/2005 Drmanac et al. ................ 435/6

OTHER PUBLICATIONS

Erlich et al., "STI1 Promotes Glioma Proliferation Through MAPK and PI3K Pathways," *GLIA* 55, 1690-1698 (2007).
Lopes et al., "Interaction of Cellular Prion and Stress-Inducible Protein 1 Promotes Neuritogenesis and Neuroprotection by Distinct Signaling Pathways," *The Journal of Neuroscience* 25(49), 11330-11339 (2005).
Blatch et al., "Isolation of a mouse cDNA encoding mSTI1, a stress-inducible protein containing the TPR motif," *GENE* 194, 277-282 (1997).
Honore et al., "Molecular Cloning and Expression of a Transformation-sensitive Human Protein Containing the TPR Motif and Sharing Identity to the Stress-inducible Yeast Protein *STI1*," *The Journal of Biological Chemistry* 267, 8485-8491 (1992).
Americo et al., "Signaling induced by hop/STI-1 depends on endocytosis," *BBRC* 358, 620-625 (2007).
Zanata et al., "Stress-inducible protein 1 is a cell surface ligand for cellular prion that triggers neuroprotection," *The EMBO Journal* 21, 3307-3316 (2002).

* cited by examiner

*Primary Examiner* — Alana Harris Dent
(74) *Attorney, Agent, or Firm* — White & Case LLP

(57) ABSTRACT

The invention is based on the discovery that STI1/Hop promotes proliferation of human glioblastoma-derived cells but not of normal astrocytes and that the proliferation requires the binding of STI1/Hop to $PrP^c$. The invention is directed to methods for treating cancer which rely on interfering with the Hop-$PrP^c$ interaction and to peptides, and antibodies raised against the peptides, which directly provide that interference. The invention is further based on the discovery that $STI1_{230-245}$ peptide and its human homologue Hop230-245 provide the desired interference with the STI1/Hop-$PrP^c$ interaction and inhibit the STI1/Hop-induced proliferation of glioma and glioblastoma cells. The invention is thus further directed to methods of treating cancer that employ these peptides and functional derivatives thereof, and antibodies directed to the peptides and derivatives. The invention is further directed to means of treating cancer which involve reducing the effective amount of Hop or reducing the expression of Hop. The invention is further directed to means of alleviating or eliminating the side effects of drug therapy and radiotherapy used in treating patients with brain cancers.

6 Claims, 14 Drawing Sheets

SEQUENCE LISTING

<160> NUMBER OF SEQ ID NOS: 13

<210> SEQ ID NO 1
<211> LENGTH: 16
<212> TYPE: PRT
<213> ORGANISM: Mus musculus

<400> SEQUENCE: 1

Glu Leu Gly Asn Asp Ala Tyr Lys Lys Lys Asp Phe Asp Lys Ala Leu
1               5                   10                  15

<210> SEQ ID NO 2
<211> LENGTH: 16

```
<212> TYPE: PRT
<213> ORGANISM: Homo sapiens

<400> SEQUENCE: 2

Glu Leu Gly Asn Asp Ala Tyr Lys Lys Asp Phe Asp Thr Ala Leu
1               5                   10                  15

<210> SEQ ID NO 3
<211> LENGTH: 16
<212> TYPE: PRT
<213> ORGANISM: Homo sapiens

<400> SEQUENCE: 3

Gly Cys Lys Thr Val Asp Leu Lys Pro Asp Trp Gly Lys Gly Tyr Ser
1               5                   10                  15

<210> SEQ ID NO 4
<211> LENGTH: 21
<212> TYPE: DNA
<213> ORGANISM: Artificial Sequence
<220> FEATURE:
<223> OTHER INFORMATION: primer sequence

<400> SEQUENCE: 4
cctgggcacg aaactacaag a                                          21

<210> SEQ ID NO 5
<211> LENGTH: 21
<212> TYPE: DNA
<213> ORGANISM: Artificial Sequence
<220> FEATURE:
<223> OTHER INFORMATION: primer sequence

<400> SEQUENCE: 5
gcaatctctt cctcctcatc c                                          21

<210> SEQ ID NO 6
<211> LENGTH: 543
<212> TYPE: PRT
<213> ORGANISM: Homo sapiens

<400> SEQUENCE: 6

Met Glu Gln Val Asn Glu Leu Lys Glu Lys Gly Asn Lys Ala Leu Ser
1               5                   10                  15

Val Gly Asn Ile Asp Asp Ala Leu Gln Cys Tyr Ser Glu Ala Ile Lys
                20                  25                  30

Leu Asp Pro His Asn His Val Leu Tyr Ser Asn Arg Ser Ala Ala Tyr
            35                  40                  45

Ala Lys Lys Gly Asp Tyr Gln Lys Ala Tyr Glu Asp Gly Cys Lys Thr
        50                  55                  60

Val Asp Leu Lys Pro Asp Trp Gly Lys Gly Tyr Ser Arg Lys Ala Ala
65                  70                  75                  80

Ala Leu Glu Phe Leu Asn Arg Phe Glu Glu Ala Lys Arg Thr Tyr Glu
                85                  90                  95

Glu Gly Leu Lys His Glu Ala Asn Asn Pro Gln Leu Lys Glu Gly Leu
            100                 105                 110

Gln Asn Met Glu Ala Arg Leu Ala Glu Arg Lys Phe Met Asn Pro Phe
        115                 120                 125

Asn Met Pro Asn Leu Tyr Gln Lys Leu Glu Ser Asp Pro Arg Thr Arg
    130                 135                 140

Thr Leu Leu Ser Asp Pro Thr Tyr Arg Glu Leu Ile Glu Gln Leu Arg
```

```
            145                 150                 155                 160
Asn Lys Pro Ser Asp Leu Gly Thr Lys Leu Gln Asp Pro Arg Ile Met
                165                 170                 175

Thr Thr Leu Ser Val Leu Leu Gly Val Asp Leu Gly Ser Met Asp Glu
            180                 185                 190

Glu Glu Glu Ile Ala Thr Pro Pro Pro Pro Pro Lys Lys Glu
        195                 200                 205

Thr Lys Pro Glu Pro Met Glu Glu Asp Leu Pro Glu Asn Lys Lys Gln
    210                 215                 220

Ala Leu Lys Glu Lys Glu Leu Gly Asn Asp Ala Tyr Lys Lys Asp
225                 230                 235                 240

Phe Asp Thr Ala Leu Lys His Tyr Asp Lys Ala Lys Glu Leu Asp Pro
                245                 250                 255

Thr Asn Met Thr Tyr Ile Thr Asn Gln Ala Ala Val Tyr Phe Glu Lys
            260                 265                 270

Gly Asp Tyr Asn Lys Cys Arg Glu Leu Cys Glu Lys Ala Ile Glu Val
        275                 280                 285

Gly Arg Glu Asn Arg Glu Asp Tyr Arg Gln Ile Ala Lys Ala Tyr Ala
    290                 295                 300

Arg Ile Gly Asn Ser Tyr Phe Lys Glu Lys Tyr Lys Asp Ala Ile
305                 310                 315                 320

His Phe Tyr Asn Lys Ser Leu Ala Glu His Arg Thr Pro Asp Val Leu
                325                 330                 335

Lys Lys Cys Gln Gln Ala Glu Lys Ile Leu Lys Glu Gln Glu Arg Leu
            340                 345                 350

Ala Tyr Ile Asn Pro Asp Leu Ala Leu Glu Glu Lys Asn Lys Gly Asn
        355                 360                 365

Glu Cys Phe Gln Lys Gly Asp Tyr Pro Gln Ala Met Lys His Tyr Thr
    370                 375                 380

Glu Ala Ile Lys Arg Asn Pro Lys Asp Ala Lys Leu Tyr Ser Asn Arg
385                 390                 395                 400

Ala Ala Cys Tyr Thr Lys Leu Leu Glu Phe Gln Leu Ala Leu Lys Asp
                405                 410                 415

Cys Glu Glu Cys Ile Gln Leu Glu Pro Thr Phe Ile Lys Gly Tyr Thr
            420                 425                 430

Arg Lys Ala Ala Ala Leu Glu Ala Met Lys Asp Tyr Thr Lys Ala Met
        435                 440                 445

Asp Val Tyr Gln Lys Ala Leu Asp Leu Asp Ser Ser Cys Lys Glu Ala
    450                 455                 460

Ala Asp Gly Tyr Gln Arg Cys Met Met Ala Gln Tyr Asn Arg His Asp
465                 470                 475                 480

Ser Pro Glu Asp Val Lys Arg Arg Ala Met Ala Asp Pro Glu Val Gln
                485                 490                 495

Gln Ile Met Ser Asp Pro Ala Met Arg Leu Ile Leu Glu Gln Met Gln
            500                 505                 510

Lys Asp Pro Gln Ala Leu Ser Glu His Leu Lys Asn Pro Val Ile Ala
        515                 520                 525

Gln Lys Ile Gln Lys Leu Met Asp Val Gly Leu Ile Ala Ile Arg
    530                 535                 540

<210> SEQ ID NO 7
<211> LENGTH: 543
<212> TYPE: PRT
<213> ORGANISM: Mus musculus
```

<400> SEQUENCE: 7

```
Met Glu Gln Val Asn Glu Leu Lys Glu Lys Gly Asn Lys Ala Leu Ser
1               5                   10                  15

Ala Gly Asn Ile Asp Asp Ala Leu Gln Cys Tyr Ser Glu Ala Ile Lys
            20                  25                  30

Leu Asp Pro Gln Asn His Val Leu Tyr Ser Asn Arg Ser Ala Ala Tyr
        35                  40                  45

Ala Lys Lys Gly Asp Tyr Gln Lys Ala Tyr Glu Asp Gly Cys Lys Thr
50                  55                  60

Val Asp Leu Lys Pro Asp Trp Gly Lys Gly Tyr Ser Arg Lys Ala Ala
65                  70                  75                  80

Ala Leu Glu Phe Leu Asn Arg Phe Glu Glu Ala Lys Arg Thr Tyr Glu
                85                  90                  95

Glu Gly Leu Lys His Glu Ala Asn Asn Leu Gln Leu Lys Glu Gly Leu
            100                 105                 110

Gln Asn Met Glu Ala Arg Leu Ala Glu Arg Lys Phe Met Asn Pro Phe
        115                 120                 125

Asn Leu Pro Asn Leu Tyr Gln Lys Leu Glu Asn Asp Pro Arg Thr Arg
130                 135                 140

Ser Leu Leu Ser Asp Pro Thr Tyr Arg Glu Leu Ile Glu Gln Leu Gln
145                 150                 155                 160

Asn Lys Pro Ser Asp Leu Gly Thr Lys Leu Gln Asp Pro Arg Val Met
                165                 170                 175

Thr Thr Leu Ser Val Leu Leu Gly Val Asp Leu Gly Ser Met Asp Glu
            180                 185                 190

Glu Glu Glu Ala Ala Thr Pro Pro Pro Pro Pro Lys Lys Glu
        195                 200                 205

Pro Lys Pro Glu Pro Met Glu Glu Asp Leu Pro Glu Asn Lys Lys Gln
210                 215                 220

Ala Leu Lys Glu Lys Glu Leu Gly Asn Asp Ala Tyr Lys Lys Lys Asp
225                 230                 235                 240

Phe Asp Lys Ala Leu Lys His Tyr Asp Arg Ala Lys Glu Leu Asp Pro
                245                 250                 255

Thr Asn Met Thr Tyr Ile Thr Asn Gln Ala Ala Val His Phe Glu Lys
            260                 265                 270

Gly Asp Tyr Asn Lys Cys Arg Glu Leu Cys Glu Lys Ala Ile Glu Val
        275                 280                 285

Gly Arg Glu Asn Arg Glu Asp Tyr Arg Gln Ile Ala Lys Ala Tyr Ala
290                 295                 300

Arg Ile Gly Asn Ser Tyr Phe Lys Glu Lys Tyr Lys Asp Ala Ile
305                 310                 315                 320

His Phe Tyr Asn Lys Ser Leu Ala Glu His Arg Thr Pro Asp Val Leu
                325                 330                 335

Lys Lys Cys Gln Gln Ala Glu Lys Ile Leu Lys Glu Gln Glu Arg Leu
            340                 345                 350

Ala Tyr Ile Asn Pro Asp Leu Ala Leu Glu Glu Lys Asn Lys Gly Asn
        355                 360                 365

Glu Cys Phe Gln Lys Gly Asp Tyr Pro Gln Ala Met Lys His Tyr Thr
370                 375                 380

Glu Ala Ile Lys Arg Asn Pro Arg Asp Ala Lys Leu Tyr Ser Asn Arg
385                 390                 395                 400

Ala Ala Cys Tyr Thr Lys Leu Leu Glu Phe Gln Leu Ala Leu Lys Asp
```

```
            405                 410                 415
Cys Glu Glu Cys Ile Gln Leu Glu Pro Thr Phe Ile Lys Gly Tyr Thr
        420                 425                 430

Arg Lys Ala Ala Ala Leu Glu Ala Met Lys Asp Tyr Thr Lys Ala Met
        435                 440                 445

Asp Val Tyr Gln Lys Ala Leu Asp Leu Asp Ser Ser Cys Lys Glu Ala
    450                 455                 460

Ala Asp Gly Tyr Gln Arg Cys Met Met Ala Gln Tyr Asn Arg His Asp
465                 470                 475                 480

Ser Pro Glu Asp Val Lys Arg Arg Ala Met Ala Asp Pro Glu Val Gln
            485                 490                 495

Gln Ile Met Ser Asp Pro Ala Met Arg Leu Ile Leu Glu Gln Met Gln
        500                 505                 510

Lys Asp Pro Gln Ala Leu Ser Glu His Leu Lys Asn Pro Val Ile Ala
        515                 520                 525

Gln Lys Ile Gln Lys Leu Met Asp Val Gly Leu Ile Ala Ile Arg
    530                 535                 540

<210> SEQ ID NO 8
<211> LENGTH: 11
<212> TYPE: PRT
<213> ORGANISM: Human immunodeficiency virus

<400> SEQUENCE: 8

Tyr Gly Arg Lys Lys Arg Arg Gln Arg Arg Arg
1               5                   10

<210> SEQ ID NO 9
<211> LENGTH: 27
<212> TYPE: PRT
<213> ORGANISM: Artificial Sequence
<220> FEATURE:
<223> OTHER INFORMATION: conjugate of seq id nos: 1 and 8

<400> SEQUENCE: 9

Tyr Gly Arg Lys Lys Arg Arg Gln Arg Arg Arg Glu Leu Gly Asn Asp
1               5                   10                  15

Ala Tyr Lys Lys Lys Asp Phe Asp Lys Ala Leu
            20                  25

<210> SEQ ID NO 10
<211> LENGTH: 27
<212> TYPE: PRT
<213> ORGANISM: Artificial Sequence
<220> FEATURE:
<223> OTHER INFORMATION: conjugate of seq id nos: 2 and 8

<400> SEQUENCE: 10

Tyr Gly Arg Lys Lys Arg Arg Gln Arg Arg Arg Glu Leu Gly Asn Asp
1               5                   10                  15

Ala Tyr Lys Lys Lys Asp Phe Asp Thr Ala Leu
            20                  25

<210> SEQ ID NO 11
<211> LENGTH: 19
<212> TYPE: PRT
<213> ORGANISM: Artificial Sequence
<220> FEATURE:
<223> OTHER INFORMATION: derived from C-terminal portion of human
      aprotinin

<400> SEQUENCE: 11
```

```
Thr Phe Phe Tyr Gly Gly Cys Arg Gly Lys Arg Asn Asn Phe Lys Thr
1               5                   10                  15

Glu Glu Tyr

<210> SEQ ID NO 12
<211> LENGTH: 35
<212> TYPE: PRT
<213> ORGANISM: artificial sequence
<220> FEATURE:
<223> OTHER INFORMATION: conjugate of seq id nos: 2 and 11

<400> SEQUENCE: 12

Thr Phe Phe Tyr Gly Gly Cys Arg Gly Lys Arg Asn Asn Phe Lys Thr
1               5                   10                  15

Glu Glu Tyr Glu Leu Gly Asn Asp Ala Tyr Lys Lys Lys Asp Phe Asp
            20                  25                  30

Thr Ala Leu
        35

<210> SEQ ID NO 13
<211> LENGTH: 35
<212> TYPE: PRT
<213> ORGANISM: artificial sequence
<220> FEATURE:
<223> OTHER INFORMATION: conjugate of seq id nos: 1 and 11

<400> SEQUENCE: 13

Thr Phe Phe Tyr Gly Gly Cys Arg Gly Lys Arg Asn Asn Phe Lys Thr
1               5                   10                  15

Glu Glu Tyr Glu Leu Gly Asn Asp Ala Tyr Lys Lys Lys Asp Phe Asp
            20                  25                  30

Lys Ala Leu
        35
```

PEPTIDES AND METHODS FOR THE TREATMENT OF GLIOMAS AND OTHER CANCERS

This application claims the benefit of U.S. Provisional Application No. 60/972,958, filed Sep. 17, 2007.

BACKGROUND OF THE INVENTION

Gliomas are tumors derived from glia or their precursors within the central nervous system. Malignant gliomas, the most common subtype of primary brain tumors, are aggressive, highly invasive and neurologically destructive. Clinically, gliomas are divided into four grades and the most aggressive of these, grade IV astrocytoma or glioblastoma multiforme (GBM), is also the most common in humans (Kleihues 2000; Maher et al. 2001). Despite maximum treatment efforts, median survival of patients diagnosed with GBM ranges from 9 to 12 months, a statistic that has changed very little in decades. Primary brain tumors, like all cancers, share a relatively restricted set of characteristics crucial to their phenotype: proliferation in the absence of external growth stimuli, avoidance of apoptosis and no limits to replication, escape from both external growth-suppressive forces and the immune response, formation of new blood vessels and the ability to invade normal tissues (Hanahan and Weinberg 2000). Furthermore, despite their striking heterogeneity, common alterations in specific cellular signal transduction pathways occur within most GBMs. Deregulation of signal transduction, which accounts for aberrant responses to distinct soluble factors, is also a common feature of these tumors, and modulation of signaling pathways has become an option for targeted therapies (Sebolt-Leopold and Herrera 2004).

Previous work from our group (Zanata et al. 2002) identified the co-chaperone stress-inducible phosphoprotein 1 (STI1) as a cell-surface ligand for the membrane glycosylphosphatidylinositol (GPI) anchored cellular prion ($PrP^C$), which leads to the activation of several signal transduction pathways, some of which modulate cell survival. Stress-inducible phosphoprotein 1 (STI1), also referred to, in the case of the human homologue, as Hop (Hsp70/Hsp90 organizing protein), is a 66 kDa protein first identified in yeast and originally described as a co-chaperone that binds to both Hsp70 and Hsp90, and regulates their activities (Chen and Smith 1998; Nicolet and Craig 1989; Song and Masison 2005). Due to the 98% sequence homology between the mouse (STI1) and human (Hop) molecules (Table 1), the term STI1/Hop will be used throughout this disclosure as the designation for the protein. In cases where the intention is to specify either the mouse or human homologue, the respective designation STI1 or Hop alone will be made.

STI1/Hop is present in diverse cellular locations, exists within nuclear transcription complexes, is able to move dynamically between the cytoplasm and the nucleus (Odunuga et al. 2004) and although it lacks a transmembrane domain or a signal peptide for membrane transport, it is also present at the cell surface (Martins et al. 1997; Zanata et al. 2002). In fact, many proteins expected to be confined in the cytoplasm are also at the cell surface where they play specific functions, in particular as receptors for plasma proteins (Nickel 2005). Previous work had already showed that STI1/Hop involvement in Hsp90-independent complexes relates to diverse cellular events such as transcription, protein folding and translocation, viral replication, signal transduction and cell division (Odunuga et al. 2004). STI1/Hop was shown to be secreted by normal astrocytes (Lima et al. 2007) and by HT-1080 fibrosarcoma cells together with other chaperones and co-chaperones, suggesting that these proteins may form extracellular active Hsp90 complexes related to MMP2 (metalloproteinase 2) activation and consequent tumor invasiveness (Eustace and Jay 2004; Eustace et al. 2004). Another study also related the activity of Hsp90, an STI1/Hop partner, to a molecular mechanism of tumor response selectivity to geldanamycin (Kamal et al. 2003).

Previous work from our group showed that a cellular prion-binding peptide designed on the basis of the complementary hydropathy theory (Boquet et al. 1995; Brentani 1988; Martins et al. 1997), later identified as a domain of STI1/Hop (Zanata et al. 2002), was able to activate the PKA and Erk signaling pathways, with the former being associated with cell survival in retinal explants (Chiarini et al. 2002). In addition, recombinant STI1/Hop was reported to modulate retinal proliferation and cell death (Arruda-Carvalho et al. 2007), to trigger neuroprotection and neuritogenesis in hippocampal neurons through PKA and MAPK pathways, respectively (Lopes et al. 2005) and to induce endocytosis-dependent MAPK signaling (Americo et al. 2007; Caetano et al. 2008).

BRIEF SUMMARY OF THE INVENTION

The invention is based on the discovery that STI1 promotes proliferation of human glioblastoma-derived cells but not of normal astrocytes and that the proliferation requires the binding of STI1/Hop to $PrP^C$. The invention is directed to methods for treating cancer which rely on interfering with the STI1/Hop-$PrP^C$ interaction and to peptides, and antibodies raised against the peptides, which directly provide that interference.

The invention is further based on the discovery that $STI1_{230-245}$ peptide and its human homologue $Hop_{230-245}$ provide the desired interference with the STI1/Hop-$PrP^C$ interaction and inhibit the STI1/Hop-induced proliferation of glioma and glioblastoma cells. The invention is thus further directed to methods of treating cancer that employ these peptides and functional derivatives thereof, and antibodies directed to the peptides and derivatives.

The invention is further directed to means of treating cancer which involve reducing the effective amount of STI1/Hop or reducing the expression of STI1/Hop.

The invention is still further directed to use of the disclosed peptides in diminishing and even eliminating the side effects of standard treatments given patients with brain cancer.

DETAILED DESCRIPTION OF THE INVENTION

Materials and Methods

Chemicals

Figure 1A:
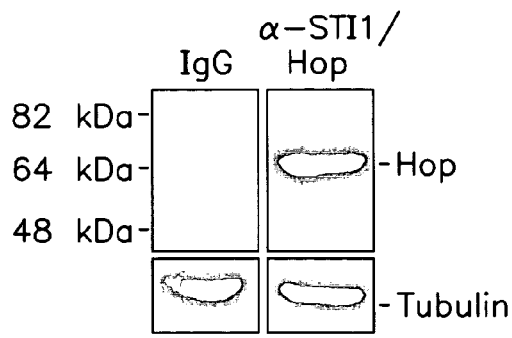
FIGS. 1A-1D depict the results of experiments showing secretion of Hop by A172 cells and the consequent proliferation of cells.

U0126, LY294002 and Forskolin were obtained from Sigma (USA). Some of the drug preparations were made in cell-culture-grade dimethylsulfoxide (DMSO) (Sigma, USA). The final concentrations of DMSO in the culture medium in all experiments were a maximum of 0.4% (v/v). [$^3$H]-thymidine was obtained from IPEN/CNEN (Brazil). Rabbit IgG was obtained from Sigma (USA). Polyclonal antibodies recognizing total Akt, phosphorylated Akt (Ser 473), phosphorylated p44/p42 MAPK, tubulin and peroxidase-conjugated anti-rabbit IgG secondary antibody were obtained from Cell Signaling (USA). Polyclonal antibody recognizing Erk2 was obtained from Santa Cruz (USA). Polyclonal antibody recognizing STI1/Hop was obtained from Bethyl (USA) (Zanata et al. 2002). Polyclonal antibody recognizing GFAP was obtained from Dako (USA). A polyclonal antibody recognizing PrP$^C$ raised in Prnp knock-out mice was produced at Ludwig Institute for Cancer Research, São Paulo (Brazil) (Lee et al. 2001). Chemicals and reagents were analytical grade or better.

Maintenance of Cell Lines

The A172, U87-MG, C6 and MCF7 tumor-cell lines were obtained from ATCC (American Type Culture Collection) and were grown and maintained in Dulbecco's modified Eagle medium-F12, supplemented with glucose (33 mM, Merck), glutamine (2 mM, Calbiochem), sodium bicarbonate (3 mM, Merck), penicillin/streptomycin (0.5 mg/ml), Fungizone (2.5 ug/ml, Squibb) and fetal bovine serum 10% (v/v) (Gibco). Culture flasks were maintained at 37° C. in 5% CO$_2$ and 95% air. Exponentially growing cells were detached from the culture flasks with 0.25% trypsin/ethylenediaminetetraacetic acid (EDTA) and seeded at different densities depending on the assay.

Astrocyte Cultures

Primary astrocytes were obtained from Wistar rats. The cerebral hemispheres were dissected and the meninges carefully removed. During dissection the tissue was maintained in a PBS-0.6% glucose solution. Thereafter the tissue was mechanically dissociated and centrifuged in a clinical centrifuge. The supernatant was removed, the pellet resuspended in DMEM-F12 with 10% FBS and the cells seeded in flask cultures. The culture media was changed every other day. Once the cultures became semi-confluent, they were washed with PBS, detached from the culture flasks with 0.25% trypsin/ethylenediaminetetraacetic acid (EDTA) and seeded at different densities depending on the assay.

Western Blotting

After the treatments described herein, cells were washed twice with cold phosphate-buffered saline (PBS) and lysed in 1% NP40, 1% Triton X-100, 1% Sodium Deoxycholate, 10 mM Tris-HCl pH 7.5, 100 mM NaCl, 0.1% SDS, 5 mM EDTA, supplemented with Complete protease and phosphatase inhibitory cocktails (Roche, USA). Samples (30-40 μg) were resolved by SDS-PAGE and transferred to a nitrocellulose membrane. The membranes were blocked with 5% nonfat milk in Tris-buffered saline, 0.1% Tween-20 (TBS-T) for one hour, incubated with primary antibodies (STI1/Hop 0.5 μg/ml purified IgG, phospho-Erk 1:1000, phospho-Akt 1:1000, Erk2 1:5000, Akt 1:1000, tubulin 1:1000) overnight at 4° C., washed with TBS-T and incubated with horseradish peroxidase-conjugated secondary antibodies (1:2000) for one hour. The reactions were developed using enhanced chemiluminescence (Pierce, USA). The conditioned media (CM) from A172 cells were filtered to remove cell debris and concentrated in an Amicon apparatus (Amicon, USA) before electrophoresis. Western blotting assays for CM were conducted using anti-STI1/Hop (0.5 μg/ml) antibody.

Immunodepletion Assay

A172-CM was incubated with rabbit anti-STI1/Hop antibody (4 μg/ml) overnight at 4° C., mixed with CL-4B Sepharose (Pharmacia, USA) for 2 h at 4° C. and then centrifuged. The pellet and the supernatant (CM depleted of STI1/Hop) were analyzed for the presence of STI1/Hop.

Immunocytochemistry

A172 tumor cells and rat astrocytes were seeded at 5×10$^4$ cells per well on glass slides in 24-well plates and cultured for 24 hours in serum-free culture media. Then the culture media was removed and the cells were fixed with 4% paraformaldehyde in phosphate buffer for 30 seconds. Fixed cells were washed with PBS and then incubated with a solution of 1% bovine serum albumin (BSA) in PBS for 1 hour. Thereafter, the cells were incubated with serum anti-STI1/Hop (1:200 in 1% BSA) or anti-GFAP (1:1000 in 1% BSA) antibodies for 16 hours at 4° C., washed again with PBS and incubated with the Cy-3- or FITC-conjugated secondary antibodies (1:500 in PBS) for 3 hr. Then the cells were washed with PBS, stained with DAPI (Sigma), washed again and mounted. For negative controls, cells received similar treatment but the primary antibodies, anti-STI1/Hop or anti-GFAP, were omitted.

Flow Cytometry Assay

Cells were grown and detached as described above. Then at least 10$^6$ cells were collected, centrifuged, resuspended in a PBS/BSA 0.5% solution and incubated with a polyclonal antibody anti-PrP$^C$ (Lee et al. 2001) (1:100) for 1 hr at room temperature (RT). Thereafter cells were washed three times with PBS, incubated with a secondary antibody for 1 hr at RT, and assayed in a BD FACScan using the Lysis II program.

Conditioned Media

Semi-confluent A172 cell cultures maintained in 75 cm$^2$ culture flasks were washed once with PBS and three times with serum-free media. Cells were cultured for 48 hr in serum-free culture media. After this period the conditioned media was collected and subjected to 5 min. centrifugation at 1500 rpm in a standard clinical centrifuge. The supernatant was collected and stored at −70° C.

Cell Viability

Cells were cultured for 24 hr in 24-well plates in serum-free media and subjected to identical treatments as in [$^3$H]-thymidine incorporation assays. Thereafter, the culture media was removed; the cells were incubated with Trypan Blue 0.2% (v/v) in PBS for 1 min. and then washed with PBS. A minimum of 5×10² cells per well in randomly selected fields were counted.

Expression and Purification of STI1

Recombinant wild-type and mutant STI1 were obtained as previously described (Lopes et al. 2005; Zanata et al. 2002). Briefly, protein expression was induced by 1.5 mM isopropyl-β-D-thiogalactopyranoside (IPTG) for 4 hr in *Escherichia Coli* DH-5α cells (Stratagene) containing the expression vector $His_6$-STI1. Cells were resuspended in lysis buffer ($Na_2HPO_4$ 50 mM, NaCl 300 mM, pH 8.0) containing protease inhibitors, and subjected to freeze-thawing cycles. Protein was purified using Ni-NTA-agarose (Qiagen) in accord with manufacturer's instructions.

Treatments

For [³H]-thymidine incorporation and cell viability assays, U0126 (10 μM), LY294002 (5 μM), Forskolin (10 μM) (Chen et al. 2003, Lee et al 2005, Shingu et al. 2003), recombinant STI1 (170 nM) and DMSO (0.4%) were added at the beginning of the 24-hr period. For western blots, cells were subjected to STI1/Hop, U0126 and LY294002 treatments as indicated in the figure legends. For co-treatments, the inhibitors were added 10 minutes prior to STI1.

Densitometries

Densitometric analyses of the immunoblots were performed using the ImageQuant software. The ratio between phospho-specific bands and their respective loading controls was calculated and the results were normalized to the respective control groups.

Proliferation Assays

Proliferation assays were conducted using [³H]-thymidine incorporation or BrdU incorporation.

a. [³H]-Thymidine Incorporation Assays

Tumor cells were subjected to a "starvation period," i.e., they were seeded at $10^4$ cells per well in DMEM-F12 serum-free in 48-well plates. Rat astrocytes were seeded at $4×10^4$ cells per well in DMEM-F12 serum-free or 5% FBS in 48-well plates. After 3 hours, the different compounds with which the cells were to be treated were added. After 18 hours of treatment, a [³H]-thymidine 6-hour pulse was added. At the end of this 24-hour period, the medium was carefully removed and 300 μl of ice-cold 10% trichloroacetic acid was added. Cells were harvested and [³H]-thymidine incorporation was measured with a scintillation counter.

b. BrdU Incorporation Assays b.1 A172 Cell Line

Cells were plated overnight on 24-well plates with glass coverslips, at a density of $1×10^4$ cells per well, in DMEM high glucose plus 10% FCS at 37° C. Plates were washed 3 times with PBS and were maintained in DMEM without FCS for 30 hours. Cells were then treated for 18 hours with DMEM/10% FCS or DMEM plus mouse recombinant STI1 (170 nM); STI1 (170 nM) plus $STI1_{230-245}$ peptide (170 nM); or STI1 (170 nM) plus $STI1_{61-76}$ irrelevant peptide (170 nM). Thirty minutes before the end of treatment, cells received a pulse of BrdU (35 μM) and were fixed with 4% paraformaldehyde.

b.2 U87MG Cell Line

Cells were plated overnight on 24-well plates with glass cover slips, at a density of $1.5×10^4$ cells per well, with DMEM with 10% FCS at 37° C. Plates were washed 3 times with PBS and were maintained in DMEM F12 for 48 hours. Cells were then treated for 24 hours with DMEM/10% FCS or DMEM plus mouse recombinant STI1 (170 nM); recombinant STI1 (170 nM) plus mouse peptide $STI1_{230-245}$(ELGN-DAYKKKDFDKAL) (SEQ ID NO: 1) or its human homologue peptide $Hop_{230-245}$(ELGNDAYKKKDFDTAL) (SEQ ID NO: 2) (170 nM or 8 μM); STI1 (170 nM) plus STI1/ $Hop_{61-76}$ (GCKTVDLKPDWGKGYS) (SEQ ID NO: 3) irrelevant peptide (170 nM or 8 μM); or each one of the peptides alone. Two hours before the end of treatment, cells received a pulse of BrdU (35 μM) pulse and were fixed with 4% paraformaldehyde.

b.3 Immunofluorescence Assay for BrdU Incorporation

Coverslips were treated with 2N HCl for 30 minutes. The reagent was then removed and borate buffer applied (boric acid 0.1M, sodium hydroxide 0.15M), pH 8.4, for 10 minutes. Then, cells were treated with PBS plus 0.2% Triton X-100 for 15 minutes. The blocking step was made with PBS/0.2% Triton with 20% horse serum, for 1 hour. Primary anti-BrdU biotinylated antibodies (1:100) were applied overnight (diluted in PBS/0.2% Triton with 1% horse serum). Coverslips were washed 3 times with PBS and incubated for one hour with Strepta-Alexa 488 and DAPI reagents (1:1000), washed more 3 times with PBS and assembled to slides.

Cell Counting

There were taken at least four microscopic fields of each treatment on WB filter, ranging from 330-385 nm (DAPI), plus their respective BrdU images, on WIB filter, 450-480 nm using DP controller software, Olympus. Picture files were analyzed on ImageJ software, and the percentage of BrdU positive nuclei in respect to total nuclei number (DAPI) was calculated using the Analyze Particles tool.

Tissue Samples

Fresh surgical samples of glioblastoma and of non-tumor tissue of the CNS (temporal lobectomy from epilepsy surgeries) were macrodissected and immediately snap-frozen in liquid nitrogen upon surgical removal. Necrotic and non-neoplastic areas were removed from the frozen block and the tumor tissue was microdissected prior to the RNA extraction procedure.

For quantitative real time RT-PCR, 17 samples of non-tumor and 76 glioblastomas from humans were evaluated.

Total RNA Isolation and cDNA Synthesis

Total RNA was extracted from normal and tumor tissues using guanidine isothiocyanate. Conventional reverse transcription was performed to obtain single-strand cDNA for real time RT-PCR.

Quantitative Real-Time RT-PCR

The STI1/Hop expression levels were determined by real time PCR analysis. Primers were designed to amplify a DNA fragment of 101-bp length. Primer sequences were as follows (5' to 3'): F:CCTGGGCACGAAACTACAAGA (SEQ ID NO: 4), R:GCAATCTCTTCCTCCTCATCC (SEQ ID NO: 5). All primers were synthesized by Sigma.

The minimum concentration of primers was determined by the lowest threshold cycle and maximum amplification efficiency while minimizing nonspecific amplification. Analysis of DNA melting curves demonstrated a single peak for both primers. The reactions consisted of: 3 μl of primer mixture (final concentration of 100 nM), 3 μl of cDNA sample, and 6 μl SYBR Green I Master Mix (Applied Biosystems). Reactions were run on an ABI Prism 5700 sequence detector (Applied Biosystems). DNA melting curve analysis showed a single peak for the STI1/Hop amplified product. Quantitative data was normalized relative to the internal housekeeping control (BCRP—Breast cancer resistance protein; HPRT-hypoxanthine-guanine phosphoribosyltransferase and GUSβ—β glucuronidase).

The $1.73^{-\Delta\Delta Ct}$ equation was applied to calculate the relative expression of Hop in tumor samples versus the median of normal CNS tissues, where $\Delta Ct = Ct\ gene - Ct\ normalized$, and $\Delta\Delta Ct = \Delta Ct\ tumor - mean\ \Delta Ct\ normal\ tissues$.

Behavioral Training of Animals in Long-Term Memory Tests

Rats were trained in a one-trial, step-down IA paradigm, a hippocampal-dependent learning task in which stepping down from a platform present in a given context is associated with a foot shock, resulting in an increase in step-down latency when the animal is brought back to the training chamber for a retention test (Cammarota et al., 2004). The IA apparatus was a 50×25×25 cm Plexiglas box with a 5-cm-high, 8-cm-wide and 25-cm-long platform on the left end of a series of bronze bars that constitutes the floor of the box. During training, each animal was gently placed on the platform facing the left rear corner of the training box. When an animal stepped down and placed all four of its paws on the grid, it received a 2-s, 0.5-mA foot shock and was then immediately withdrawn from the training box. Animals were replaced in the IA box for retention testing 90 min (for short-term memory (STM)), or 24 h later (for long-term memory (LTM)); their latency to step down onto the grid was recorded. The difference between the training and test-session step-down latencies was taken as a measure of retention. Better memory for the training was inferred from longer retention latencies (Bernabeu et al., 1997; Izquierdo et al., 1997). The maximum retention latency allowed was 180 s, at which time the animal was taken out of the IA box if it had not stepped down and given a score of 180 s. Full details of the experimental protocols can be found in Coitinho et al., 2007.

Statistical Analysis

The number of experimental replicates for each of the studies shown in FIGS. 1-6 is given in the respective figure legends. Data were analyzed by Student's t-test when two groups are compared or ANOVA followed by post-hoc comparisons (Tukey's test) when multiple groups are compared.

In proliferation assays, the mean values of at least three independent datasets are shown in the figures; the error bars represent standard error of measurement (SEM). ANOVA followed by Tukey-HSD or Dunnets tests were used for multiple comparisons. Results were considered statistically significant when p was <0.05.

For quantitative RT-PCR statistical analysis was applied to gene expression data obtained from both glioblastomas and normal CNS tissues. The Mann-Whitney test was used and the results were considered statistically significant when p was <0.05.

The data obtained in tests of the effect of peptides on rat long-term memory are presented as medians±interquartile range and were analyzed by the Kruskal-Wallis nonparametric test followed by Dunn's post-hoc (n=10 to 13 animals for each treatment group). In all comparisons, p<0.05 was taken as a significant difference.

Results

Hop is Secreted by A172 Human Glioblastoma Cell Line and Induces Proliferation.

Figure 1B:
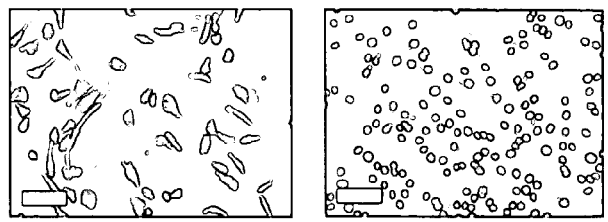

We first tested for the expression of Hop in the A172 human GBM cell line. Western blot assays of A172 total lysates probed for Hop showed a single band at the expected molecular weight (66 kDa) (FIG. 1A), and immunocytochemistry of cells cultured in serum-free media and fixed with paraformaldehyde showed extensive Hop immunolabeling (FIG. 1B).

Figure 1C:
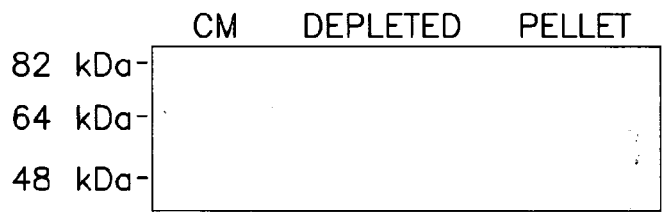
Figure 1D:
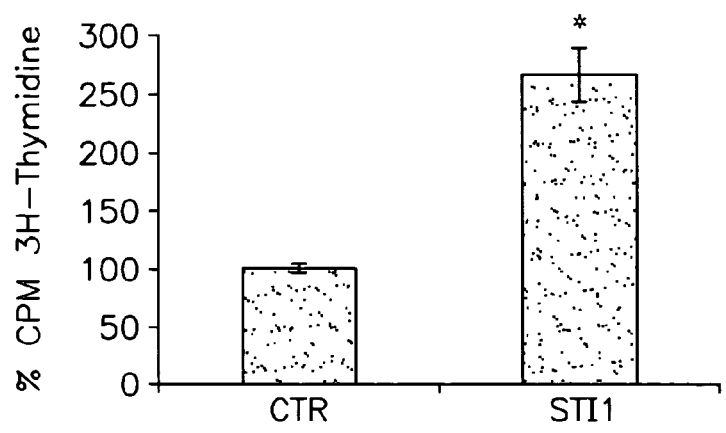

The cellular secretion of Hsp-90 as well as STI1/Hop has been previously described (Eustace and Jay 2004; Eustace et al. 2004) and results from our group (Lima et al. 2007) demonstrated that STI1/Hop is secreted from primary astrocyte cultures. We conducted western blots and immunoprecipitation assays and demonstrated the presence of Hop in conditioned medium from A172 cells (FIG. 1C; CM). Hop was immunoprecipitated from CM using specific antibodies (FIG. 1C pellet) and depleted from the immunoprecipitation supernatant material (FIG. 1C; depleted). The lack of CD44 in the conditioned medium also confirmed the absence of cell lysis. Therefore, these data demonstrated that Hop is secreted from the A172 glioma cell line.

Figure 5A:
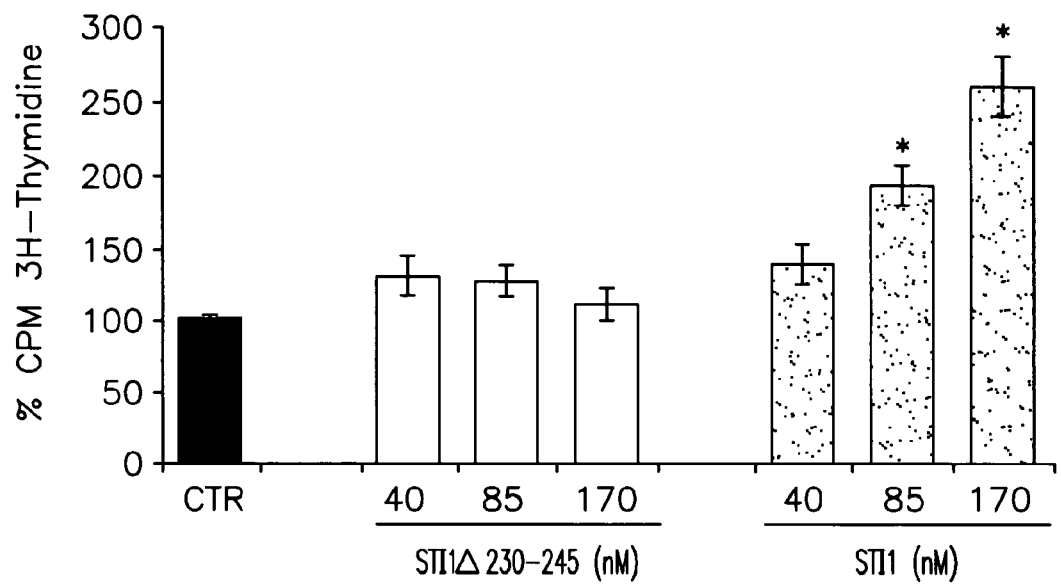
FIGS. 5A and B are graphic depictions of experimental results showing that the $PrP^C$ binding site of STI1 is necessary for STI1-induced proliferation.

To test whether STI1/Hop modulates proliferation of a GBM cell line, we assayed [$^3$H]-thymidine incorporation in A172 cells cultured in serum-free media. Proliferation was determined by quantitative measurement of [3H]-thymidine incorporation (6.7 µCi/ml, 6-hour pulse) and the results were normalized with respect to the rate of proliferation (100%) in serum-free media (CTR). A172 cells treated with recombinant STI1 (170 nM) showed a marked increase in the uptake of thymidine, as compared with control (FIG. 1D), indicating that STI1/Hop induces proliferation of this cell line. Dose-response curves demonstrated that the STI1/Hop effect was maximum at 170 nM (FIG. 5A).

MAPK and PI3K Signaling Pathways are Involved in the STI1-Induced Proliferation of Glioma Cells.

Figure 2A:
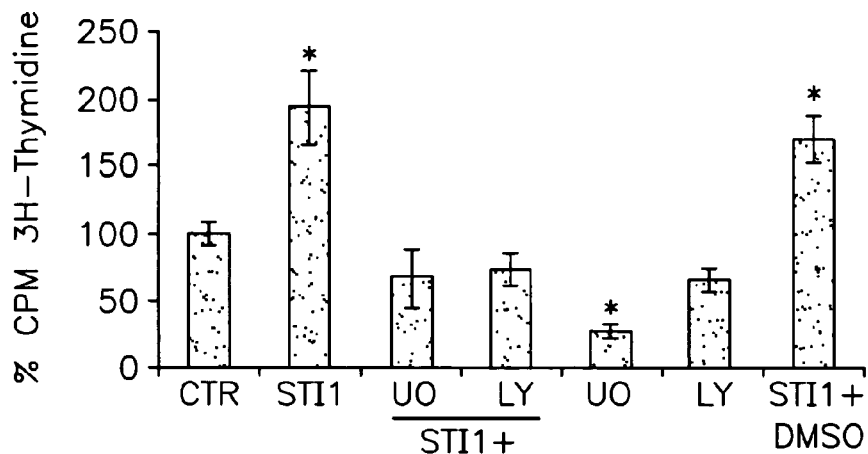
FIGS. 2A-I depict the results of experiments showing the involvement of the MAPK and PI3K pathways in STI1-induced glioma-cell proliferation.
Figure 2B:
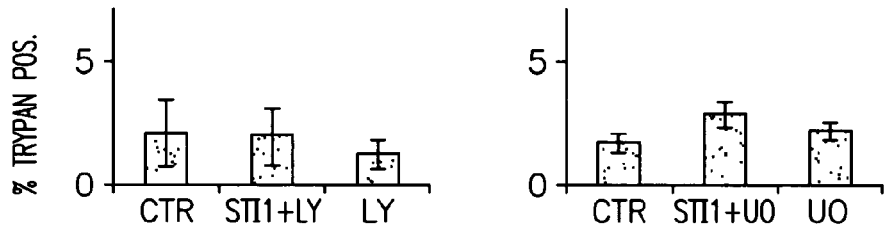

MAPK and PI3K signaling pathways commonly relate to cell proliferation and are often deregulated in cancer. In order to investigate the involvement of these pathways in STI1-induced proliferation, A172 cells were treated with STI1 in the presence of either U0126, an inhibitor of the Erk-activating kinase MEK, or LY294002, an inhibitor of PI3K. These drugs completely abolished STI1-induced proliferation, which suggests the involvement of both pathways (FIG. 2A) in this phenotype. Cell viability was always higher than 95%, ruling out possible cytotoxic effects of the inhibitors as the cause of the proliferation blockade (FIG. 2B).

Figure 2C:
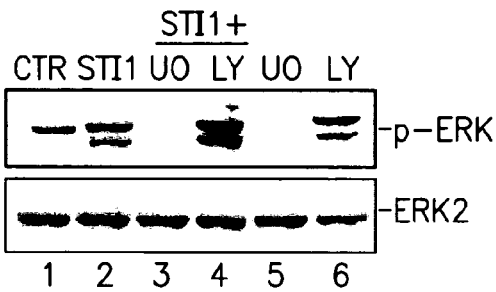
Figure 2E:
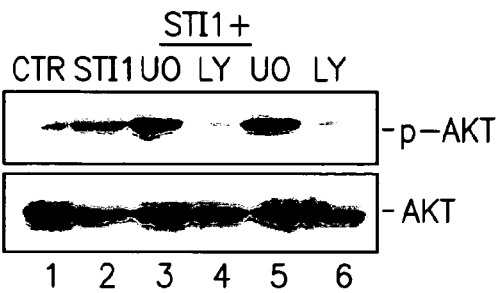
Figure 2D:
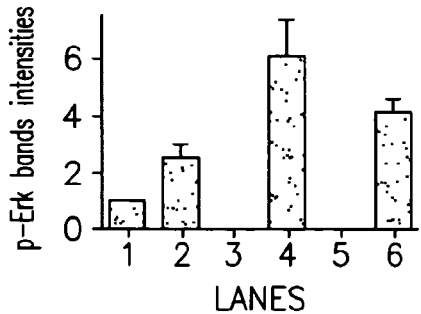
Figure 2F:
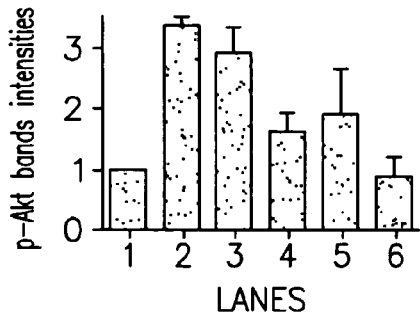

Western blots of lysates from A172 cells cultured in serum-free media confirmed that treatment with STI1 induced activation of Erk and Akt and that this effect was abolished by co-treatment with U0126 or LY294002, respectively (FIGS. 2C, D and 2E, F). Interestingly, STI1 co-treatment with LY294002 led to an increase in the phosphorylation of Erk (FIGS. 2C, D; lane 4) as compared with cells treated only with STI1 (FIG. 2C, D; lane 2).

Paradoxical effects of MAPK activation regarding not only its intensity, but also its duration have already been described (Marshall 1995; Sebolt-Leopold and Herrera 2004; Sewing et al. 1997; Sharrocks 2006). In this context, we assayed for Erk activation induced by treatment with STI1 alone, STI1 in the presence of LY294002 and LY294002 alone for 5, 35 and 60 minutes (FIGS. 2G, H). Although the levels of Erk activation in cells treated for 5 min. with LY294002 (lane 8) were similar to those in cells treated with STI1 (lane 2), Erk activity induced by the PI3K inhibitor was much more durable, lasting for at least one hour (lanes 8-10), as opposed to that seen in STI1-treated cells (lanes 2-4). STI1 treatment in the presence of the PI3K inhibitor led to an increase in the intensity and duration of Erk activity (lanes 5-7) as compared to that seen in cells treated with STI1 alone (lanes 2-4).

STI1/Hop-induced neuroprotection was previously related to PKA pathway activation (Chiarini et al. 2002; Lopes et al. 2005). In this context we tested for the effect of forskolin, an activator of adenylyl cyclase, upon incorporation of thymidine by A172 cells (FIG. 2I). Even when cultured in serum-free media, cells treated with forskolin showed a marked decrease in DNA synthesis, as compared to control group. This result suggests that the involvement of PKA in STI1/Hop-induced proliferation is unlikely.

STI1/Hop Modulates the Proliferation of Distinct Glioma Cell Lines.

Although gliomas are classified in different groups based on histological features, it is known that these tumors are constituted by a heterogeneous set of cell populations, which renders each tumor a unique pathologic process and prevents the development of broadly effective therapeutic regimens.

Figure 3:
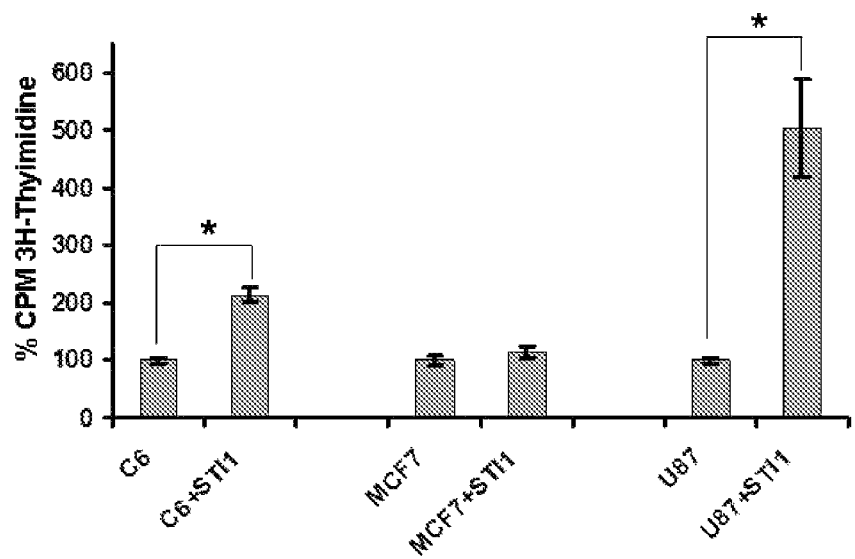
FIG. 3 is a graphic depiction of STI1-induced proliferation in distinct glioma cell lines.

To address the generality of the effect of STI1/Hop, we treated distinct tumor cell lines with STI1 and assayed for thymidine incorporation (FIG. 3). Similarly to A172 cells, both C6 and U87-MG cell lines, respectively, a rat glioma and a human GBM, were responsive to STI1 treatment, although with different intensities. On the other hand, the MCF-7 cell line, a breast adenocarcinoma, was insensitive to STI1 treatment.

STI1/Hop does not Induce Proliferation of Normal Astrocytes.

To compare with the response of the GBM cell line, normal astrocytes obtained from neonate rats cultured in serum-free media (FIG. 4A) or in media supplemented with FBS 5% (FIG. 4B) were treated with STI1, and assayed for thymidine incorporation. STI1 had no effect upon the low level of proliferation of the astrocytes cultured in serum-free medium. However, STI1 treatment produced a small but statistically significant decrease in the proliferation of astrocytes cultured in FBS 5%. The effect of FBS 5% upon astrocyte proliferation is shown in FIG. 4C. Immunocytochemistry assays confirmed the expression of GFAP in these astrocytes (FIG. 4D).

Figure 5B:
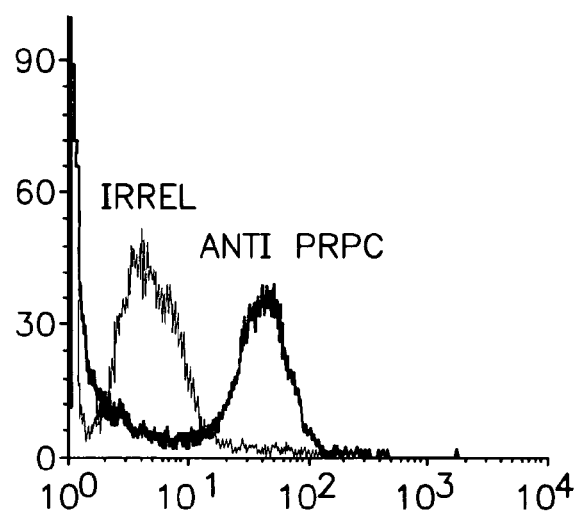

The $PrP^C$ Binding Site of STI1/Hop is Necessary for STI1-Induced Proliferation of A172 Cells Cellular prion ($PrP^C$) was previously described as an STI1/Hop receptor and also related to STI1/Hop-induced neuroprotection and differentiation (Chiarini et al. 2002; Lopes et al. 2005; Zanata et al. 2002). To investigate a possible role of $PrP^C$ in the proliferative effect of STI1/Hop, we performed thymidine incorporation assays in A172 cells treated with distinct concentrations of a mouse STI1 mutant lacking residues 230-245 ($STI1\Delta_{230-245}$) (Lopes et al. 2005) whose deleted domain was previously characterized as the $PrP^C$ binding site (Zanata et al. 2002). While wild-type STI1 promoted proliferation of glioma cells, the mutant STI1 did not promote proliferation (FIG. 5A). Flow cytometry confirmed the presence of $PrP^C$ at the surface of viable A172 cells (FIG. 5B). These data indicate a role for $PrP^C$ in STI1/Hop-induced proliferation of A172 cells.

The Use of $STI1_{230-245}$ Peptide to Block STI1/Hop-Dependent Glioma Proliferation In light of the observations disclosed above, we have identified mouse $STI1_{230-245}$ and other related peptides as candidates for effectively inhibiting the proliferation of human gliomas and other cancers triggered by the interaction between STI1/Hop and $PrP^C$. Accordingly, we undertook various additional investigations into the effect of such peptides on glioma-cell proliferation.

The proliferation was assessed by bromodeoxyuridine (BrdU) incorporation, followed by immunofluorescence imaging and cell counting. The "starvation" period confers a better interval for observation of the effects of the studied factor (STI1/Hop) and the hypothetical inhibitors $STI1_{230-245}$ and $Hop_{230-245}$ peptides. Additionally, the BrdU assay affords a more reliable proliferation evaluation, in which it is possible to observe the morphology and integrity of cells, and documentation (microscope imaging). While a thymidine incorporation assay best exhibits speed of DNA synthesis, by indirect CPM counting, a BrdU incorporation assay is more objective, allowing the measurement of the number of cells synthesizing DNA and deduction of the percentage of cells under proliferation. For these reasons, we selected the BrdU/DAPI ratio of positive nuclei as the analysis method.

$STI1_{230-245}$ Peptide Abrogates STI1-Induced Proliferation

Figure 7A:
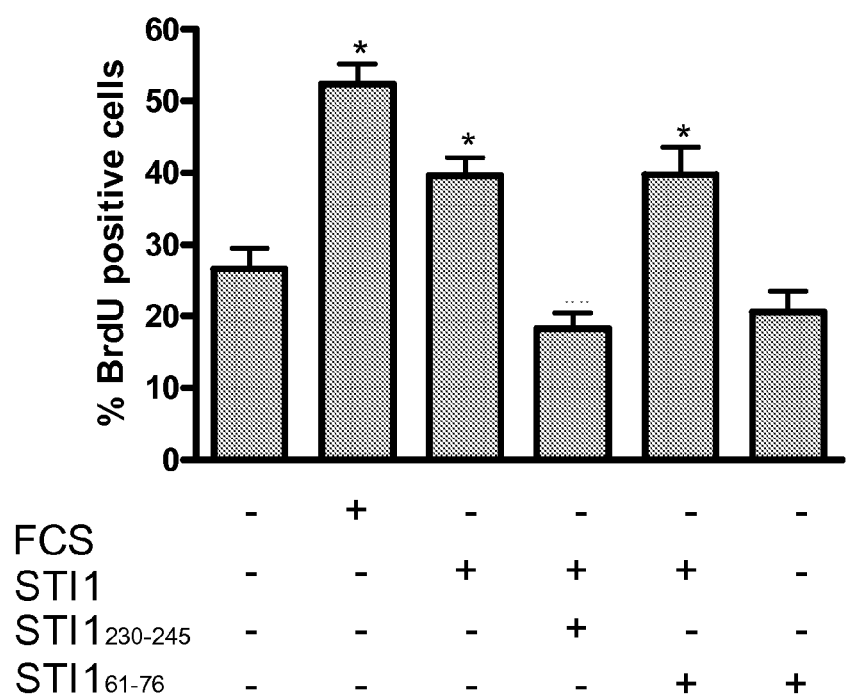
FIGS. 7A and B are graphic depictions of experimental results showing that STI1$_{230-245}$ peptide abrogates STI1-induced proliferation of glioma cell lines.

Similarly to the previously described findings (Erlich et al., 2007), STI1 was observed to produce a 1.5-fold increase on A172 cell proliferation. On the other hand, mouse $STI1_{230-245}$ peptide (ELGNDAYKKKDFDKAL) at the same concentration of STI1 (170 nM) inhibited STI1-induced proliferation, while N-terminus irrelevant STI1/Hop peptide ($STI1/Hop_{61-76}$) had no effect on STI1-mediated proliferation (FIG. 7A).

Figure 6:
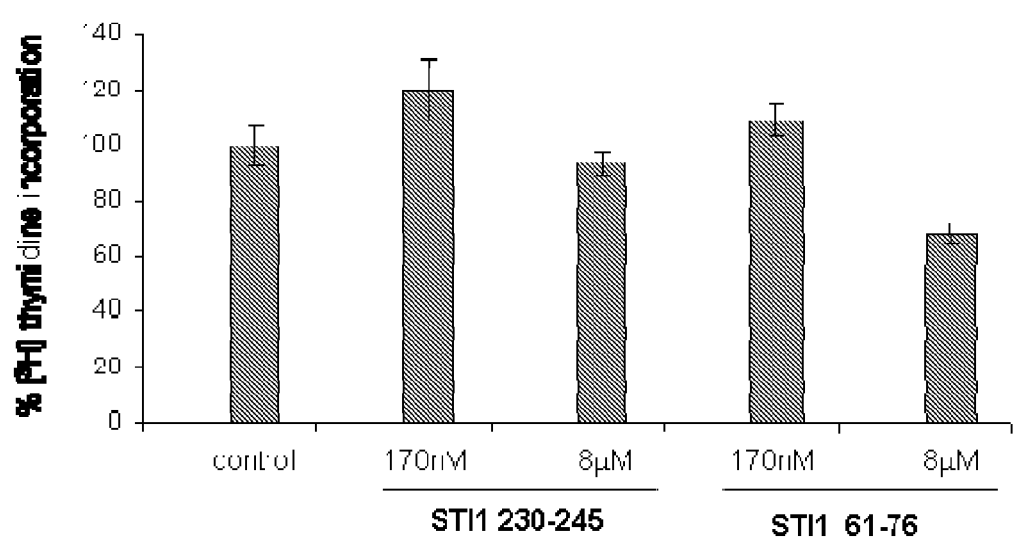
FIG. 6 is a graphic depiction of experimental results showing that $STI1_{230-245}$ peptide does not promote proliferation of A172 cells.

FIG. 6 depicts the results of what served as a control study; the effect of $STI1_{230-245}$ alone on proliferation of A172 cells was monitored. As can be seen from this figure, $STI1_{230-245}$ was unable by itself to promote proliferation of A172 cells. It can also be seen in FIG. 6 that N-terminal irrelevant peptide $STI1_{61-76}$ did not enhance proliferation.

We observed that STI1 treatment promoted a 3-fold increase of U87MG proliferation, which was blocked by the $STI1_{230-245}$ peptide at 170 nM and 8 μM but not by the irrelevant $STI1/Hop_{61-76}$ peptide. The sequences of the $STI1_{61-76}$ and $Hop_{61-76}$ peptides are the same (see Table 1). Experimental data are summarized in FIG. 7B.

U87MG cells presented a slower doubling time (48 hours) than A172 and were very sensitive to serum starvation. Thus they were starved in DMEM F12 for this purpose (Brockmann et al., 2003).

$Hop_{230-245}$ Peptide Inhibits STI1-Induced Proliferation

Furthermore, we addressed whether the human homologue of mouse $STI1_{230-245}$ peptide—$Hop_{230-245}$ (ELGN-DAYKKKDFDTAL)—could modulate proliferation in U87MG cells. The homology between STI1 and Hop peptides is shown in the side-by-side comparison of the two full sequences in Table 1.

Figure 8:
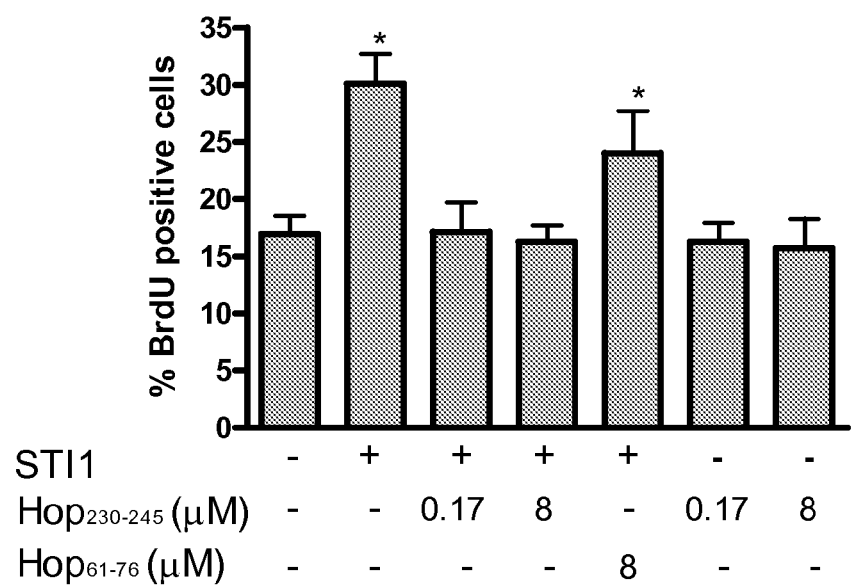
FIG. 8 is a graphic depiction of experimental results showing that Hop$_{230-245}$ peptide inhibits STI1-induced proliferation of A172 cells.

The data in FIG. 8 show that $Hop_{230-245}$ peptide, as well as its mouse counterpart ($STI1_{230-245}$), were able to abrogate the cell proliferation mediated by STI1. The N-terminal irrelevant peptide, $STI1/Hop_{61-76}$, had no effect upon proliferation mediated by STI1.

Taken together, these data validate the use of the human counterpart of $STI1_{230-245}$ peptide ($Hop_{230-245}$) to block STI1-induced proliferation.

TABLE 1

Homology between n STI1 and Hop amino acid sequences (98%)

HUMAN-Hop
MOUSE-STI1

```
  1  MEQVNELKEK  GNKALSVGNI  DDALQCYSEA  IKLDPHNHVL
     YSNRSAAYAK  KGDYQKAYED

1  MEQVNELKEK  GNKALSAGNI  DDALQCYSEA  IKLDPQNHVL
     YSNRSAAYAK  KGDYQKAYED

61  GCKTVDLKPD  WGKGYSRKAA  ALEFLNRFEE  AKRTYEEGLK
     HEANNPQLKE  GLQNMEARLA

61  GCKTVDLKPD  WGKGYSRKAA  ALEFLNRFEE  AKRTYEEGLK
     HEANNLQLKE  GLQNMEARLA

121  ERKFMNPFNM  PNLYQKLESD  PRTRTLLSDP  TYRELIEQLR
     NKPSDLGTKL  QDPRIMTTLS

121  ERKFMNPFNL  PNLYQKLEND  PRTRSLLSDP  TYRELIEQLQ
     NKPSDLGTKL  QDPRVMTTLS

181  VLLGVDLGSM  DEEEEIATPP  PPPPPKKETK  PEPMEEDLPE
     NKKQALKEKE  LGNDAYKKKD

181  VLLGVDLGSM  DEEEEAATPP  PPPPPKKEPK  PEPMEEDLPE
     NKKQALKEKE  LGNDAYKKKD
```

TABLE 1-continued

Homology between n STI1 and Hop amino acid sequences (98%)

```
241 PDTALKHYDK AKELDPTNMT YITNQAAVYF EKGDYNKCRE
    LCEKAIEVGR ENREDYRQIA

241 PDKALKHYDR AKELDPTNMT YITNQAAVHF EKGDYNKCRE
    LCEKAIEVGR ENREDYRQIA

301 KAYARIGNSY FKEEKYKDAI HFYNKSLAEH RTPDVLKKCQ
    QAEKILKEQE RLAYINPDLA

301 KAYARIGNSY FKEEKYKDAI HFYNKSLAEH RTPDVLKKCQ
    QAEKILKEQE RLAYINPDLA

361 LEEKNKGNEC FQKGDYPQAM KHYTEAIKRN PKDAKLYSNR
    AACYTKLLEF QLALKDCEEC

361 LEEKNKGNEC FQKGDYPQAM KHYTEAIKRN PKDAKLYSNR
    AACYTKLLEF QLALKDCEEC

421 IQLEPTFIKG YTRKAAALEA MKDYTKAMDV YQKALDLDSS
    CKEAADGYQR CMMAQYNRHD

421 IQLEPTFIKG YTRKAAALEA MKDYTKAMDV YQKALDLDSS
    CKEAADGYQR CMMAQYNRHD

481 SPEDVKRRAM ADPEVQQIMS DPAMRLILEQ MQKDPQALSE
    HLKNPVIAQK IQKLMDVGLI

481 SPEDVKRRAM ADPEVQQIMS DPAMRLILEQ MQKDPQALSE
    HLKNPVIAQK IQKLMDVGLI

541 AIR       (SEQ ID NO: 6)

541 AIR       (SEQ ID NO: 7)
```

Therapeutic Use of STI1/Hop$_{230-245}$ Peptide to Treat GBM. TAT-STI1$_{230-245}$ and TAT-Hop$_{230-245}$ Peptides are Able to Block Cell Proliferation Mediated by STI1

Figure 9:
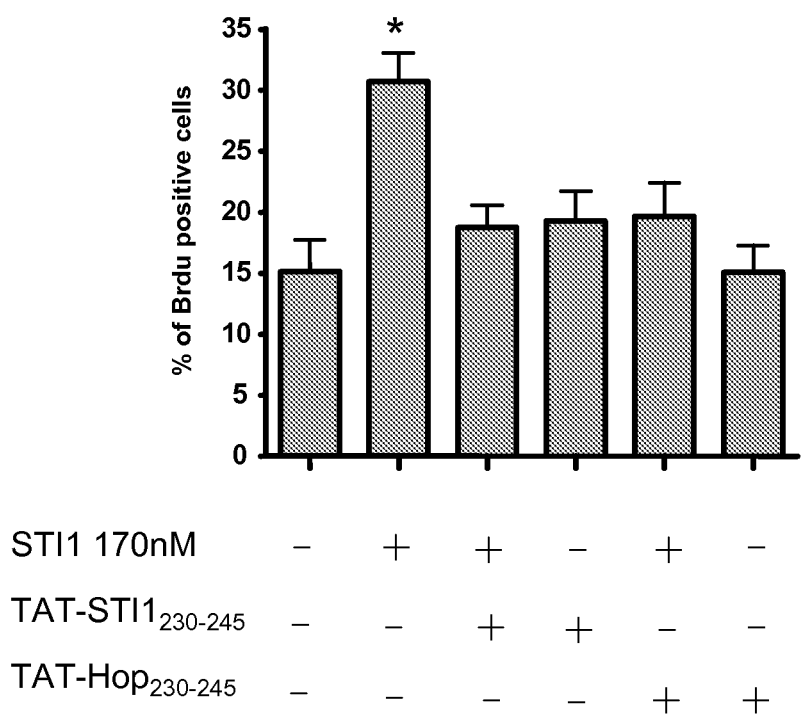
FIG. 9 is a graphic depiction of the results of experiments designed to test the therapeutic efficacy of TAT-conjugated forms of STI1$_{230-245}$ and Hop$_{230-245}$ peptides in inhibiting STI1-induced proliferation.

Since a primary objective was to implicate STI1/Hop230-245 peptides as candidates for a therapeutic approach to GBM, an alternative method for attaining optimal distribution on the brain and for reaching tumor cells became crucial. Therefore, for this purpose, STI1 and Hop peptides were conjugated to a TAT peptide sequence (YGRKKRRQRRR) (SEQ ID NO: 8), a membrane transduction domain of the HIV-1 Tat protein which permits proteins or peptides to cross the blood-brain barrier (Fawell et al., 2006; Cai et al., 2006). The biological activity of the TAT-STI1$_{230-245}$ (YGRKKRRQRRRELGNDAYKKKDFDKAL) (SEQ ID NO: 9) and TAT-Hop$_{230-245}$ (YGRKKRRQRRRELGN-DAYKKKDFDTAL) (SEQ ID NO: 10) peptides on U87 proliferation mediated by STI1/Hop was tested. FIG. 9 shows that similarly to the STI1$_{230-245}$ and Hop$_{230-245}$ peptides, TAT-STI1$_{230-245}$ and TAT-Hop$_{230-245}$ peptides were able to block cell proliferation mediated by STI1. Indeed, it was observed that the fusion of TAT peptide to the STI1$_{230-245}$ and Hop$_{230-245}$ peptides did not change their inhibitory activity on STI1-mediated glioblastoma-cell proliferation.

The TAT Peptide Allows the STI1$_{230-245}$ Peptide to Cross the Cell Membrane

Another requirement for in vivo validation of TAT-STI1$_{230-245}$ peptide effects on tumor xenografts is the study of peptide bioavailability, tissue distribution and half-life. To observe this and, especially, to confirm that TAT-STI1$_{230-245}$ is diffusible and crosses the cell membrane, we conjugated a dansyl chloride fluorophore (Aarts et al., 2002; Brebner et al., 2005) to the TAT-STI1$_{230-245}$ peptide.

Figure 10:
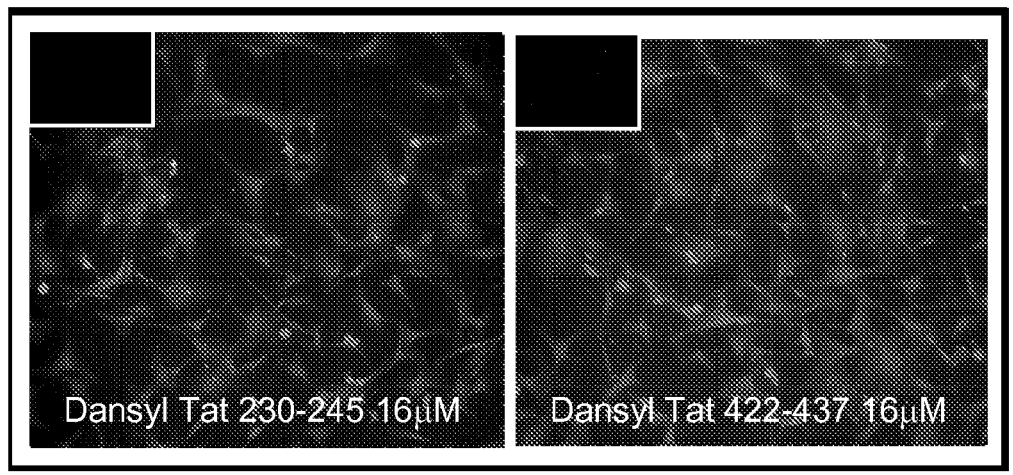
FIG. 10 shows by fluorescence microscope imaging, tests of the ability of dansylated TAT-STI1$_{230-245}$ and TAT-STI1$_{422-437}$ peptides to cross the cell membrane.

We assessed the U87MG-cell staining pattern of the dansyl-TAT-STI1$_{230-245}$ peptide and the irrelevant dansyl-TAT-STI1$_{422-437}$ peptide, as demonstrated in FIG. 10. The peptides were able to cross the cell membrane and they labeled cells efficiently.

STI1/Hop$_{230-245}$ Peptide and its TAT-Associated Forms Promote Increase in Memory Formation and can be Used as Neuroprotective Agents Against Cognitive Deficits in Patients with Brain Tumors.

The improvement in treatments of patients with brain cancer has led to a higher survival rate. However, it has also increased cognitive deficits, particularly because of side effects of drugs and radiotherapy. The use of agents designed to protect neurons against apoptosis or neurodegeneration is an interesting approach to be considered (Gehring et al., 2008). Previous studies suggested that STI1$_{230-245}$ peptide was able to promote neuronal survival (Chiarini et al., 2002; Zanata et al., 2002), neuronal differentiation (Lopes et al., 2005) and long-term memory (LTM) consolidation in rats (Coitinho et al., 2007). As demonstrated in the present studies, while inhibiting proliferative activity in tumors derived from glia cells (FIGS. 7 to 9), the peptides STI1$_{230-245}$ and Hop$_{230-245}$, as well as their counterparts associated to TAT peptide (TAT-STI1$_{230-245}$ and TAT-Hop$_{230-245}$), have a potent effect in memory consolidation in rats (FIG. 11) due to their ability to protect neurons.

Therefore, the STI1/Hop$_{230-245}$ peptides can have a dual effect in the treatment of glioblastomas. The first one is to decrease tumor proliferation mediated by secreted STI1/Hop and the second one is its protective effects in neurons and improvement in patients' cognition.

Hop is Highly Expressed in GBM Patients

Additionally, we investigated the Hop gene expression profile from 76 human glioblastoma samples using quantitative RT-PCR. It was observed that glioblastoma multiforme (GBM) expressed higher Hop levels (FIG. 12) when compared to normal tissue. These results are particularly significant because they demonstrate the connection between STI1/Hop expression and cancerous states in vivo, i.e., in human tissue samples and not just in cancer cell lines growing in culture.

Besides the TAT peptide described above, other molecules that allow drugs to cross the blood-brain barrier (BBB) have been proposed. These molecules can bind to receptors which are responsible for maintaining the integrity of the BBB and brain homeostasis. One important receptor in this regard is the lipoprotein receptor-related protein (LRP), which possesses the ability to mediate transport of ligands across endothelial cells of the BBB (Shibata et al., 2000, and Ito et al., 2006). The peptide called Angiopep-1 (TFFYGGCRGKRN-NFKTEEY) (SEQ ID NO: 11), an aprotinine-derived peptide, is able to bind LRP and promote drug delivery in the CNS (Demeule et al., 2008). Angiopep-1 has been recently conjugated to paclitaxel, and improved therapeutic efficacy was observed in orthotopic models of primary and metastatic brain cancer (Régina et al., 2008). Conjugation of STI1$_{230-245}$ and Hop$_{230-245}$ with Angiopep-1 and other peptides involved in transport across the BBB would also provide enhanced bioavailability of the peptides of the present invention to the site(s) of brain cancer in a patient.

It is also known that peptide cyclization can enhance stability without the loss of biological activity. (Pakkala et al., 2007; Yokoyama et al., 2004). This approach can be used with STI1$_{230-245}$ and Hop$_{230-245}$ peptides and their conjugates as disclosed herein to enhance their stability.

In addition, we have established a colony of nude (immunosuppressed) mice that is currently under expansion. These animals will be used to perform glioblastoma-cell engraftment and to evaluate the role of STI1$_{230-245}$ and Hop$_{230-245}$ peptides, and their TAT-associated counterparts, on tumor growth and survival. Due to the fact that they are more readily accepted in xenograft models and due to their capacity for tumorigenesis, U87MG cells will be used instead of A172 cells for these studies. It is anticipated that the results from these studies will provide further support for the notion that the inventive peptides have use as agents for the treatment of brain cancers and other cancers linked with the interaction between $PrP^C$ and STI1/Hop.

Our studies showed that: 1) Hop is secreted by a glioblastoma cell line; 2) STI1 induces proliferation of distinct glioma cell lines; 3) the Erk and Akt signaling pathways mediate STI1-induced proliferation; 4) STI1 does not induce proliferation in normal astrocytes; 5) STI1-induced proliferation of A172 cells depends on its $PrP^C$ binding domain; 6) both $STI1_{230-245}$ and $Hop_{230-245}$ peptides inhibit STI1-induced proliferation of A172 and U87MG cells; 7) the TAT-conjugates of $STI1_{230-245}$ and $Hop_{230-245}$ also inhibit glioblastoma cell proliferation; 8) conjugation of the peptides with TAT allows them to cross the cell membrane, most importantly the blood-brain barrier; 9) the $STI1_{230-245}$ peptide and its TAT conjugate enhance cognition in vivo; and 10) high expression of the Hop gene is associated with glioblastoma tissue.

Pharmacological blockade of the protein kinases Mek and PI3K abolished activation of Erk and Akt, respectively, and STI1/Hop-induced proliferation of A172 cells. In addition, treatment with STI1/Hop activated Erk and Akt, indicating the involvement of these signaling pathways in the proliferative effect. Treatment with LY294002 induced an increase in the phosphorylation levels of Erk, a finding that suggests the existence of crosstalk between these pathways (Corradetti and Guan 2006). Although activation of MAPK pathways is commonly related to an increase in proliferation, paradoxical effects of MAPK activation regarding its duration and intensity have already been described (Marshall 1995; Sewing, Wiseman et al. 1997; Sebolt-Leopold and Herrera 2004; Murphy and Blenis 2006; Sharrocks 2006). In addition, previous studies showed that Akt activation may cause downregulation of the MAPK pathway (Guan et al. 2000; Moelling et al. 2002; Zimmermann and Moelling 1999).

We showed that STI1/Hop imposes a small and transient activation of Erk, which leads to increased proliferation. On the other hand, when PI3K was inhibited, STI1/Hop-induced activation of Erk was more intense and durable, possibly because in this situation Erk pathway activity was not counterbalanced by Akt. In fact, this pattern of Erk activation may cause cell cycle arrest (Bottazzi et al. 1999; Pumiglia and Decker 1997). Cells subjected to treatment solely with LY294002 or STI1/Hop showed a similar increase in Erk activation as assayed after a 5-minute treatment. However, as opposed to the effect of STI1/Hop treatment on cells, the PI3K inhibitor induced a much more durable Erk activation, which persisted for at least one hour and was not related to increase in proliferation. Together, these data indicate that parallel activation of both the Erk and Akt pathways is required for the proliferative effects of STI1/Hop and that the intensity and duration of Erk activation may ultimately determine the final effect of STI1/Hop on proliferation. A direct involvement of the PKA pathway in the proliferative effect of STI1/Hop is unlikely, because a) upregulation of the cAMP/PKA pathway inhibits proliferation in A172 cells (Chen et al. 1998) and b) our experiments showed that forskolin induces a marked decrease in the incorporation of thymidine.

We showed that distinct tumor-cell lineages respond in distinct ways to STI1 treatment. It is noteworthy that MCF7 cells, the only non-glial tumor cell line tested, in which PTEN function is not disrupted, was not affected by STI1. It is reasonable to conclude that at least part of the distinct STI1 effects on different types of tumor-cell lines are correlated to distinct mechanisms of cell signaling regulation.

The contrast in effect of STI1/Hop upon proliferation in tumor-cell lines and normal glia proliferation is pivotal. These data suggest that drugs capable of disrupting proliferation induced by STI1/Hop would present some kind of selectivity towards tumor cells. In a completely distinct context, Kamal et al. (2003) showed that the increased activity of Hsp90, commonly observed in cancers, and probably responsible for an observed tumor response selectivity to the antibiotic geldanamicin, is explained by the formation of multichaperone complexes (including STI1/Hop) in tumors but not in normal tissues.

Prions are proteins identified as the etiologic agents of transmissible spongiform encephalopathies, a group of rare neurodegenerative diseases (Prusiner 1998). Although the precise mechanism that leads to the characteristic neurodegeneration observed in these diseases is not fully understood, abundant evidence supports the idea that the expression of cellular prion ($PrP^C$), the nonpathological isoform of the protein, and its conversion to a pathological conformer, are necessary for development of the disease (Bueler et al. 1993). The neurotoxic property acquired by the pathological isoform compared to the normal protein raised the gain-of-function hypothesis. However, loss of function of the normal $PrP^C$, caused by its conversion to the pathological isoform, may also contribute to the pathogenesis of prion diseases (Aguzzi and Weissmann 1997; Hetz et al. 2003; Samaia and Brentani 1998). In the last decade, many studies have related $PrP^C$ to distinct physiological functions (Aguzzi and Polymenidou 2004; Martins et al. 2001; Linden et al. 2008).

It has been demonstrated that $PrP^C$ is overexpressed in gastric cancer tissues, and its levels are positively correlated to the process of invasiveness and metastasis (Pan et al. 2006). In gastric cancer cell lines, $PrP^C$ promotes invasion and metastasis through activation of the Mek/Erk pathway and consequent transactivation of MMP11 (Pan et al. 2006). Moreover, $PrP^C$ ectopic expression promotes tumorigenesis, proliferation and G1/S transition in gastric cancer cells (Liang et al. 2007).

Our data showed that, as opposed to the wild-type recombinant protein, a deletion mutant STI1 which does not bind $PrP^C$ (Lopes et al. 2005) was unable to promote glioma proliferation. These data indicate that endogenous $PrP^C$ is involved in STI1/Hop-induced proliferation of gliomas.

As shown by the disclosure herein, STI1 induces the proliferation of glioma cells but not of normal astrocytes. Furthermore, the $PrP^C$ binding site of STI1/Hop is necessary to achieve this effect. Still further, a mutant STI1 missing the $PrP^C$ binding site fails to induce proliferation.

Our studies have further demonstrated that peptides $STI1_{230-245}$ and $Hop_{230-245}$, and their TAT-conjugates, inhibit the previously demonstrated ability of STI1 to enhance proliferation of glioma cells. The extension of the significance of these effects beyond the context of cell cultures, particularly in connection with the TAT-conjugated peptides, was performed in experiments testing the diffusion and ability of the conjugates to cross the cell membrane. The experiments summarized in FIG. 11 suggested that the peptides did cross the BBB, thus indicating the potential of the peptides in an in vivo context.

Further studies on trained rats treated with $STI1_{230-245}$ and TAT-$STI1_{230-245}$ showed that these peptides greatly enhanced long-term memory; animals treated with these peptides showed significantly longer retention latencies than were seen for control animals and those treated with (irrelevant) TAT-STI1$_{61-76}$ peptide.

Accordingly, one aspect of the present invention is a method for treating gliomas which involves interfering with the interaction between STI1/Hop and PrP$^C$. In one embodiment, this could involve administration of a peptide that mimics the PrP$^C$ binding site of STI1/Hop. Another embodiment would involve reduction of the effective amounts of STI1/Hop, either by a) administering a compound that targets STI1/Hop and interferes with its proliferative function or b) administering a molecule such as an siRNA that interferes with expression of STI1/Hop.

Among the peptides to be used in the practice of the invention are ELGNDAYKKKDFDTAL, ELGNDAYKKKDFDKAL, YGRKKRRQRRRELGNDAYKKKDFDTAL and YGRKKRRQRRRELGNDAYKKKDFDKAL (STI1$_{230-245}$, Hop$_{230-245}$ and their respective TAT conjugates). However, the invention is by no means limited to these exemplary peptides. For example, additional peptides to be used in the practice of the invention are cyclized versions of the ones recited above. Still further examples are TFFYGGCRGKRNNFKTEEYELGNDAYKKKDFDTAL (SEQ ID NO: 12) and TFFYGGCRGKRNNFKTEEYELGNDAYKKKDFDKAL (SEQ ID NO: 13) (the STI1$_{230-245}$ and Hop$_{230-245}$ peptides conjugated to Angiopep-1) and cyclized forms thereof. The invention also encompasses functional variants of these peptides and other peptides capable of mimicking the PrP$^C$ binding site of STI1/Hop. By functional variants are meant, for example, derivatives of the peptides, and their cyclized forms, containing one or more amino-acid additions, deletions, insertions or substitutions, or combinations of these changes. The invention is not limited to STI1/Hop peptides and functional variants thereof conjugated to TAT or Angiopep-1. It is expected that the invention can also be practiced with any STI1/Hop conjugate, wherein the peptide conjugated to the STI1/Hop enables crossing of the BBB. The peptides of the invention can be produced by any of the means of synthesis well known to those of skill in the art (see, e.g., Merrifield and Stewart 1965).

Another aspect of the invention concerns antibodies raised against peptides that mimic the PrP$^C$ binding site of STI1/Hop. Such antibodies could be raised against, for example, the peptides disclosed above, as well as against functional variants of these peptides and other peptides capable of mimicking the PrP$^C$ binding site of STI1/Hop. Such antibodies could also be used in the treatment of cancers triggered by the interaction between STI1/Hop and PrP$^C$. Such antibodies may be produced by any of the techniques well known to one of skill in the art. (See, for example, Monoclonal Antibodies: Methods and Protocols, R. Rose and M. Albitar, Eds., Humana Press, 1$^{st}$ Edition (2007) and Antibodies: A Laboratory Manual, Harlow and Love, Cold Spring Harbor Laboratory Press (2003).) Although monoclonal antibodies are preferred for the practice of the invention, the invention also encompasses polyclonal antibodies of suitable specificity.

The invention is not limited to the treatment of gliomas. It is well known that STI1/Hop is also overexpressed in, for example, the colon and the stomach. Thus, the methods of the present invention, and the compounds to be used to practice the methods, are applicable also to the treatment of such cancers as colon cancer, colorectal cancer, gastric cancer, glioblastoma, medulloblastoma and astrocytoma.

The invention is not limited to conditions brought about by overexpression of STI1/Hop. As disclosed earlier, it would be expected that the reduction of normal levels of STI1/Hop would lead to the reduction of cancer-cell proliferation and, hence, alleviation of the cancer itself.

Another embodiment of the invention is directed to methods employing the peptides of the present invention for diminishing and even eliminating the side effects of drug therapy and radiotherapy used in treating patients with brain cancers. Such side effects include neuronal death and loss of neuronal differentiation. They further include diminished cognitive function, for example reduced long-term memory consolidation.

Yet another aspect of the invention concerns methods for identifying compounds suitable for the treatment of cancers regulated by the binding of STI1/Hop to PrP$^C$. Such methods involve monitoring test compounds for their ability to reduce STI1/Hop-PrP$^C$ interaction directly, to reduce the amount of endogenous STI1/Hop that is functional and/or to reduce the amount of STI1/Hop expressed in cancer cells or potentially cancerous cell lines.

REFERENCES

Aarts M, Liu Y, Liu L, Besshoh S, Arundine M, Gurd J W, Wang Y T, Salter M W, and Tymianski M (2002) Treatment of ischemic brain damage by perturbing NMDA receptor-PSD-95 protein interactions. Science 298: 846-850.
Aguzzi A, Polymenidou M. 2004. Mammalian prion biology: one century of evolving concepts. Cell 116(2):313-27.
Aguzzi A, Weissmann C. 1997. Prion research: the next frontiers. Nature 389(6653):795-8.
Americo T A, Chiarini L B, Linden R. 2007. Signaling induced by hop/STI1 depends on endocytosis. Biochem Biophys Res Commun 358(2):620-5.
Arruda-Carvalho M, Njaine B, Silveira M S, Linden R, Chiarini L B. 2007. Hop/STI1 modulates retinal proliferation and cell death independent of PrP$^C$. Biochem Biophys Res Commun In press.
Bernabeu R, Bevilaqua L, Ardenghi P, Bromberg E, Schmitz P, Bianchin M, Izquierdo I, Medina J H (1997). Involvement of hippocampal. cAMP/cAMP-dependent protein kinase signaling pathways in a late memory consolidation phase of aversively motivated learning in rats. Proc Natl Acad Sci USA 94(13):7041-6.
Boquet D, Dery O, Frobert Y, Grassi J, Couraud J Y. 1995. Is hydropathic complementarity involved in antigen-antibody binding? Mol Immunol 32(4):303-8.
Bottazzi M E, Zhu X, Bohmer R M, Assoian R K. 1999. Regulation of p21(cip1) expression by growth factors and the extracellular matrix reveals a role for transient ERK activity in G1 phase. J Cell Biol 146(6):1255-64.
Brebner K, Wong T P, Liu L, Liu Y, Campsall P, Gray S, Phelps L, Phillips A G, and Wang Y T (2005) Nucleus accumbens long-term depression and the expression of behavioral sensitization. Science 310:1340-1343.
Brentani R R. 1988. Biological implications of complementary hydropathy of amino acids. J Theor Biol 135(4):495-9.
Bueler H, Aguzzi A, Sailer A, Greiner R A, Autenried P, Aguet M, Weissmann C. 1993. Mice devoid of PrP are resistant to scrapie. Cell 73(7):1339-47.
Cai S R, Xu G, Becker-Hapak M, Ma M, Dowdy S F, and McLeod H L (2006). The kinetics and tissue distribution of protein transduction in mice. Eur J Pharm Sci 27:311-319.
Caetano F A, Lopes M H, Hajj G N, Machado C F, Pinto Arantes C, Magalhaes A C, Vieira Mde P, Americo T A, Massensini A R, Priola S A, Vorberg I, Gomez M V, Linden R, Prado V F, Martins V R, Prado M A (2008). Endocytosis of prion protein is required for ERK ½ signalling induced by stress-inducible protein 1. J Neurosci 28(26):6691-702

Cammarota M, Bevilaqua L R, Medina J H, Izquierdo I (2004). Retrieval does not induce reconsolidation of inhibitory avoidance memory. Learn Mem 11(5):572-8.

Chen S, Smith D F. 1998. Hop as an adaptor in the heat shock protein 70 (Hsp70) and hsp90 chaperone machinery. J Biol Chem 273(52):35194-200.

Chen T C, Hinton D R, Zidovetzki R, Hofman F M. 1998. Up-regulation of the cAMP/PKA pathway inhibits proliferation, induces differentiation, and leads to apoptosis in malignant gliomas. Lab Invest 78(2):165-74.

Chiarini L B, Freitas A R, Zanata S M, Brentani R R, Martins V R, Linden R. 2002. Cellular prion protein transduces neuroprotective signals. Embo J 21(13):3317-26.

Coitinho A S, Lopes M H, Hajj G N, Rossato J I, Freitas A R, Castro C C, Cammarota M, Brentani R R, Izquierdo I, and Martins V R (2007) Short-term memory formation and long-term memory consolidation are enhanced by cellular prion association to stress-inducible protein 1. Neurobiol Dis 26:282-290.

Corradetti M N, Guan K L. 2006. Upstream of the mammalian target of rapamycin: do all roads pass through mTOR? Oncogene 25(48):6347-60.

Demeule M, Regina A, Ché C, Poirier J, Nguyen T, Gabathuler R, Castaigne J P, Béliveau R (2008). Identification and design of peptides as a new drug delivery system for the brain. J Pharm Exp Ther 324:1064-72.

Erlich R B, Kahn S, Lima F R S, Muras A G, Martins R A P, Linden R, Chiarini L B, Martins V R, Moura Neto V (2007). STI1 promotes glioma proliferation through MAPK and PI3K pathways. Glia 55(16):1690-8.

Eustace B K, Jay D G. 2004. Extracellular roles for the molecular chaperone, hsp90. Cell Cycle 3(9):1098-100.

Eustace B K, Sakurai T, Stewart J K, Yimlamai D, Unger C, Zehetmeier C, Lain B, Torella C, Henning S W, Beste G and others. 2004. Functional proteomic screens reveal an essential extracellular role for hsp90 alpha in cancer cell invasiveness. Nat Cell Biol 6(6):507-14.

Fawell S, Seery J, Daikh Y, Moore C, Chen L L, Pepinsky B, and Barsoum J (1994) Tat-mediated delivery of heterologous proteins into cells. Proc Natl Acad Sci USA 91:664-668.

Gehring K, Sitskoorn M M, Aaronson N K, Taphoorn M J B. 2008. Interventions for cognitive deficits in adults with brain tumours. Lancet Neurology 7:548-560.

Guan K L, Figueroa C, Brtva T R, Zhu T, Taylor J, Barber T D, Vojtek A B. 2000. Negative regulation of the serine/threonine kinase B-Raf by Akt. J Biol Chem 275(35): 27354-9.

Hanahan D, Weinberg R A. 2000. The hallmarks of cancer. Cell 100(1):57-70.

Hetz C, Maundrell K, Soto C. 2003. Is loss of function of the prion protein the cause of prion disorders? Trends Mol Med 9(6):237-43.

Ito S, Ohtsuki S, Terasaki T (2006). Functional characterization of the brain-to-blood efflux clearance of human amyloid-beta peptide (1-40) across the rat blood-brain barrier. Neurosci Res 56(3):246-52.

Izquierdo I, Quillfeldt J A, Zanatta M S, Quevedo J, Schaeffer E, Schmitz P K, Medina J H (1997). Sequential role of hippocampus and amygdala entorhinal cortex and parietal cortex in formation and retrieval of memory for inhibitory avoidance in rats. Eur J Neurosci 9(4):786-93.

Kamal A, Thao L, Sensintaffar J, Zhang L, Boehm M F, Fritz L C, Burrows F J. 2003. A high-affinity conformation of Hsp90 confers tumour selectivity on Hsp90 inhibitors. Nature 425(6956):407-10.

Kleihues P, and Cavanee, W. K. 2000. World Health Organization classification of tumors of the nervous system. Lyon: IARC/WHO.

Lee K S, Magalhaes A C, Zanata S M, Brentani R R, Martins V R, Prado M A. 2001. Internalization of mammalian fluorescent cellular prion protein and N-terminal deletion mutants in living cells. J Neurochem 79(1):79-87.

Lee W C, Choi C H, Cha S H, Oh H L, Kim Y K. 2005. Role of ERK in hydrogen peroxide-induced cell death of human glioma cells. Neurochem Res 30(2):263-70.

Liang J, Pan Y, Zhang D, Guo C, Shi Y, Wang J, Chen Y, Wang X, Liu J, Guo X and others. 2007. Cellular prion protein promotes proliferation and G1/S transition of human gastric cancer cells SGC7901 and AGS. Faseb J.

Lima F R, Trentin A G, Rosenthal D, Chagas C, Moura Neto V. 1997. Thyroid hormone induces protein secretion and morphological changes in astroglial cells with an increase in expression of glia! fibrillary acidic protein. J Endocrinol 154(1):167-75.

Lima F R S, Arantes C P, Muras A G, Nomizo R, Brentani R R, Martins V R. 2007. Cellular prion protein expression in astrocytes modulates neuronal survival and differentiation. J Neurochem, published on line September 14.

Linden R, Martins V R, Prado M A, Cammarota M, Izquierdo I, Brentani R R (2008). Physiology of the prion protein. Physiol Rev 88(2):673-728.

Lopes M H, Hajj G N, Muras A G, Mancini G L, Castro R M, Ribeiro K C, Brentani R R, Linden R, Martins V R. 2005. Interaction of cellular prion and stress-inducible protein 1 promotes neuritogenesis and neuroprotection by distinct signaling pathways. J Neurosci 25(49):11330-9.

Maher E A, Furnari F B, Bachoo R M, Rowitch D H, Louis D N, Cavenee W K, DePinho R A. 2001. Malignant glioma: genetics and biology of a grave matter. Genes Dev 15(11): 1311-33.

Marshall C J. 1995. Specificity of receptor tyrosine kinase signaling: transient versus sustained extracellular signal-regulated kinase activation. Cell 80(2):179-85.

Martins V R, Graner E, Garcia-Abreu J, de Souza S J, Mercadante A F, Veiga S S, Zanata S M, Neto V M, Brentani R R. 1997. Complementary hydropathy identifies a cellular prion protein receptor. Nat Med 3(12):1376-82.

Martins V R, Mercadante A F, Cabral A L, Freitas A R, Castro R M. 2001. Insights into the physiological function of cellular prion protein. Braz J Med Biol Res 34(5):585-95.

Merrifield R B and Stewart J M. 1965. Nature 207(4996):522-523.

Moelling K, Schad K, Bosse M, Zimmermann S, Schweneker M. 2002. Regulation of Raf-Akt Cross-talk. J Biol Chem 277(34):31099-106.

Murphy L O, Blenis J. 2006. MAPK signal specificity: the right place at the right time. Trends Biochem Sci 31(5): 268-75.

Nickel W. 2005. Unconventional secretory routes: direct protein export across the plasma membrane of Mammalian cells. Traffic 6(8):607-14.

Nicolet C M, Craig E A. 1989. Isolation and characterization of STI1, a stress-inducible gene from *Saccharomyces cerevisiae*. Mol Cell Biol 9(9):3638-46.

Odunuga O O, Longshaw V M, Blatch G L. 2004. Hop: more than an Hsp70/Hsp90 adaptor protein. Bioessays 26(10): 1058-68.

Pakkala M, Hekim C, Soininen P, Leinonen J, Koistinen H, Weisell J, Stenman U H, Vepsalainen J, Narvanen A (2007). Activity and stability of human kallikrein-2-specific linear and cyclic peptide inhibitors. J Peptide Sci 13(5):348-53.

Pan Y, Zhao L, Liang J, Liu J, Shi Y, Liu N, Zhang G, Jin H, Gao J, Xie H and others. 2006. Cellular prion protein promotes invasion and metastasis of gastric cancer. Faseb J 20(11):1886-8.

Prusiner S B. 1998. Prions. Proc Natl Acad Sci USA 95(23): 13363-83.

Pumiglia K M, Decker S J. 1997. Cell cycle arrest mediated by the MEK/mitogen-activated protein kinase pathway. Proc Natl Acad Sci USA 94(2):448-52.

Regina A, Demeule M, Ché C, Lavallée I, Poirier J, Gabathuler R, Béliveau R, Castaigne J P (2008). Antitumour activity of ANG1005, a conjugate between paclitaxel and the new brain delivery vector Angiopep-2. Br J Pharmacol 155(2):185-97.

Samaia H B, Brentani R R. 1998. Can loss-of-function prion-related diseases exist? Mol Psychiatry 3(3):196-7.

Sebolt-Leopold J S, Herrera R. 2004. Targeting the mitogen-activated protein kinase cascade to treat cancer. Nat Rev Cancer 4(12):937-47.

Sewing A, Wiseman B, Lloyd A C, Land H. 1997. High-intensity Raf signal causes cell cycle arrest mediated by p21Cip1. Mol Cell Biol 17(9):5588-97.

Sharrocks A D. 2006. Cell cycle: sustained ERK signalling represses the inhibitors. Curr Biol 16(14):R540-2.

Shibata M, Yamada S, Kumar S R, Calero M, Bading J, Frangione B, Holtzman D M, Miller C A, Strickland D K, Ghiso J, Zlokovic B V (2000). Clearance of Alzheimer's amyloid-ss (1-40) peptide from brain by LDL receptor-related protein-1 at the blood-brain barrier. J Clin Invest 106(12):1489-99.

Shingu T, Yamada K, Kara N, Moritake K, Osago H, Terashima M, Uemura T, Yamasaki T, Tsuchiya M. 2003. Synergistic augmentation of antimicrotubule agent-induced cytotoxicity by a phosphoinositide 3-kinase inhibitor in human malignant glioma cells. Cancer Res 63(14):4044-7.

Song Y, Masison D C. 2005. Independent regulation of Hsp70 and Hsp90 chaperones by Hsp70/Hsp90-organizing protein Sti1 (Hop1). J Biol Chem 280(40):34178-85.

Yokoyama F, Suzuki N, Haruki M, Nixhi N, Oishi S, Fujii N, Utani A, Kleinman H K, Nomizu M (2004). Cyclic peptides from the loop region of the laminin alpha 4 chain LG4 module show enhanced biological activity over linear peptides. Biochemistry 43(42):13590-7.

Zanata S M, Lopes M H, Mercadante A F, Hajj G N, Chiarini L B, Nomizo R, Freitas A R, Cabral A L, Lee K S, Juliano M A and others. 2002. Stress-inducible protein 1 is a cell surface ligand for cellular prion that triggers neuroprotection. Embo J 21(13):3307-16.

Zimmermann S, Moelling K. 1999. Phosphorylation and regulation of Raf by Akt (protein kinase B). Science 286 (5445):1741-4.

FIGURE LEGENDS

FIG. 1: Hop is secreted by A172 human glioblastoma cell line and induces proliferation. A. Western blot from A172-cell lysate probed against STI1/Hop antibody (Bethyl) reveals a single band at the expected molecular weight (66 kDa). As an isotype control, A172-cell lysate was also probed against an irrelevant IgG. B. A172 cells cultured in serum-free culture media for 24 hr were fixed and immunolabeled with an anti-STI1/Hop antibody (Bethyl) (Left panel). The right panel represents a negative control for the anti-STI1/Hop antibody to exclude unspecific staining from the secondary antibody. Nuclei in both panels were stained with DAPI. Bar, 100 μm. C. Western blot of A172 conditioned media (CM) probed with anti-STI1/Hop (Bethyl) antibody shows a band at the expected molecular weight range. The identity of the band is confirmed by its disappearance after Hop immunodepletion of CM. The pellet resulting from immunodepletion was subjected to a western blot assay that shows Hop (Pellet). CM, integral conditioned media; depleted, immunodepleted CM. The lanes are representative of equivalent starting cell numbers. Lower bands observed in the CM and Pellet lanes correspond to protein degradation and IgG heavy chain respectively. D. A172 cells were cultured in serum-free media and subjected to STI1 treatment (170 nM) for 24 hr. Proliferation was determined as described herein. Values are mean±standard error; n=15; *$P<0.001$ versus control.

Figure 2:
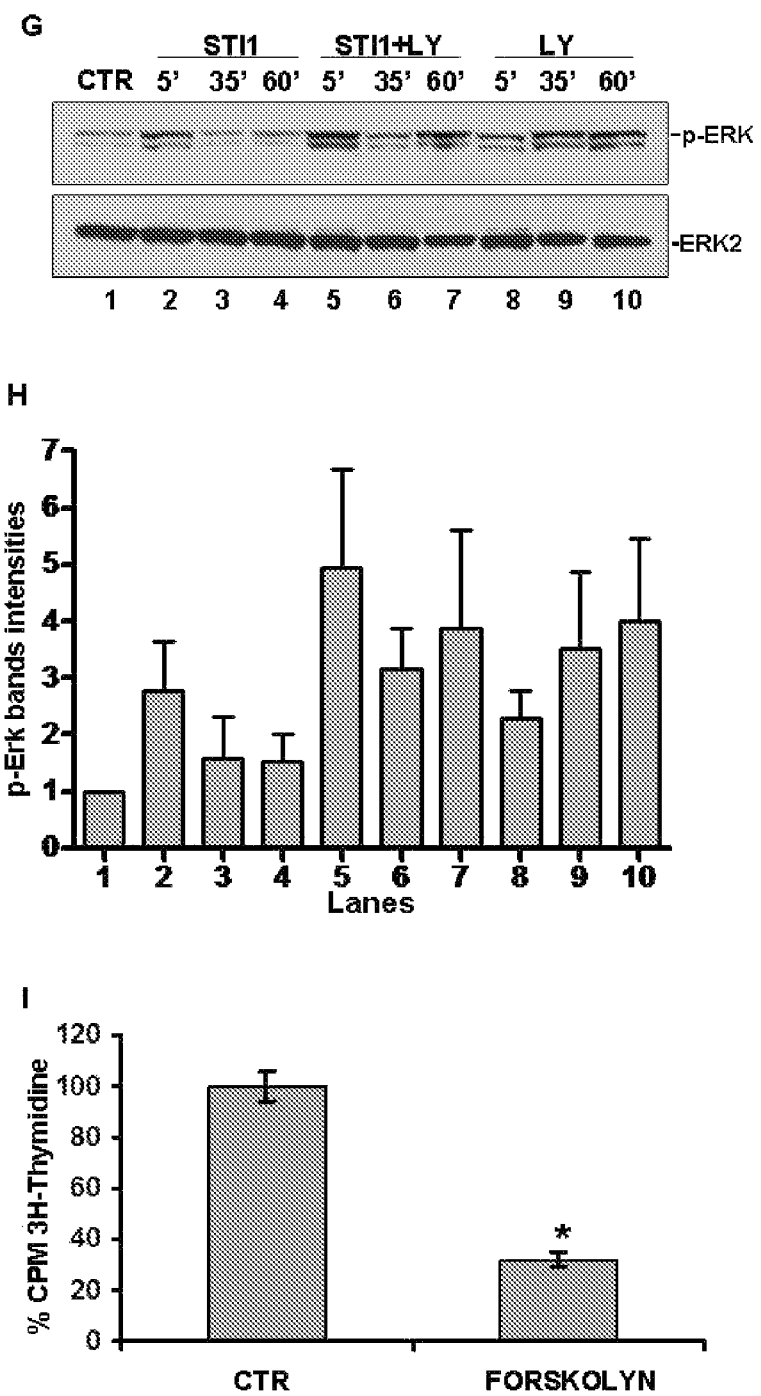

FIG. 2: MAPK and PI3K pathways are involved in STI1-induced proliferation of glioma cells. A. A172 cells were cultured in serum-free media and subjected to distinct treatments for 24 hr. Inhibitors were added 10 minutes before STI1 and abolished the STI1 effect. Proliferation was determined as described herein; n=9. *$P<0.05$ versus control. Values are mean±standard error. B. Trypan blue cell viability assay. A172 cells were cultured in serum-free media, subjected to distinct treatments for 24 hr and assayed for viability. Results are expressed as the percentage of dead cells in different experimental groups; n=9. Values are mean±standard error. C. A172 cells were subjected to STI1 treatment for 5 minutes. D. Densitometry of phospho-Erk western blots as shown in FIG. 2 C; n=3. Values are mean±standard error, normalized to untreated cells. E. A172 cells were subjected to STI1 treatment for 1 minute. F. Densitometry of phospho-Akt western blots as shown in FIG. 2 E; n=3. Values are mean±standard error, normalized to untreated cells. G. A172 cells were subjected to distinct treatments for the indicated times. H. Densitometry of phospho-Erk western blots as shown in FIG. 2 G; n=3. Values are mean±standard error, normalized to untreated cells. In co-treatments, inhibitors were added 10 minutes prior to STI1. I. A172 cells were cultured in serum-free media and subjected to forskolin treatment for 24 hr. Proliferation was determined as described herein. n=9. *$P<0.001$ versus control. Values are mean±standard error.

FIG. 3: STI1 induces proliferation in distinct glioma cell lines. Cells were cultured in serum-free media and subjected to STI1 treatment for 24 hr. Proliferation was determined by quantitative measurement of [$^3$H]-thymidine incorporation (6.7 uCi/ml, 6-hour pulse). The results are respectively normalized to the rate of proliferation (100%) in serum-free media. (CTR); n=9; C6, rat glioma; MCF7, human breast adenocarcinoma; U87, human glioblastoma. *$P<0.01$ versus control. Values are mean±standard error.

Figure 4:
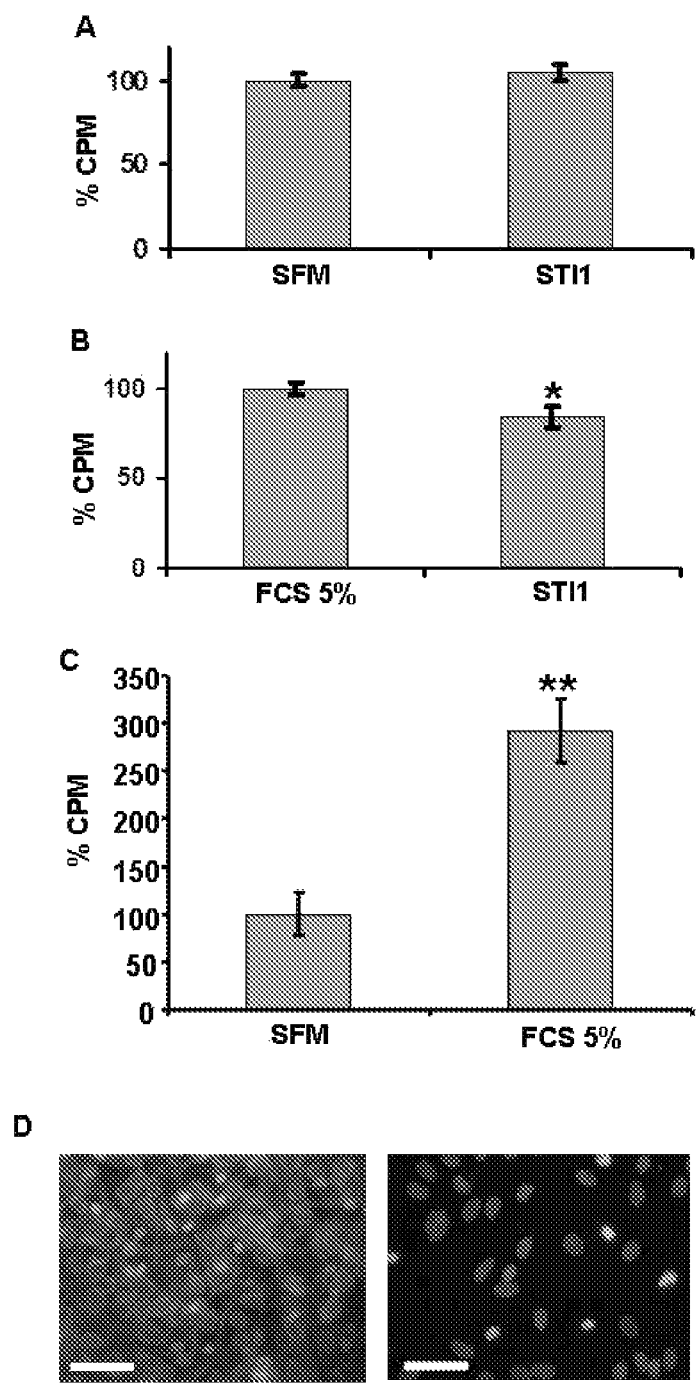
FIGS. 4A-D depict the results of experiments showing that STI1 does not induce proliferation of normal glia.

FIG. 4: STI1 does not induce proliferation in normal glia. Astrocytes obtained from neonate rats were cultured in serum-free media (A) or in 5% fetal bovine serum (FCS) (B) and subjected to STI1 treatment for 24 hr. C. FCS 5% effect upon astrocyte proliferation. Proliferation was determined as described herein. n=15; *$P<0.05$ versus control; **$P<0.001$ versus control. Values are mean±standard error. D. Astrocytes cultured in serum-free media for 48 hr were fixed and immunolabeled for GFAP (Left panel). The right panel represents a negative control for the anti-GFAP antibody to exclude unspecific staining from the secondary antibody. Nuclei in both panels were stained with DAPI. Bar, 50 μm.

FIG. 5: STI1-induced proliferation depends on its PrP$^C$ binding site. A. STI1$\Delta_{230-245}$ does not promote proliferation. Cells were cultured in serum-free media and subjected to wild-type (STI1) or mutant (STI1$\Delta_{230-245}$) treatment at distinct concentrations for 24 hr. Proliferation was determined as described herein. n=9; *$P<0.001$ versus control. Values are mean±standard error. B. Cells were incubated with an anti-PrP$^C$ antibody raised in Prnp-null mice or with an irrelevant mouse IgG for negative control. Flow cytometry assay shows PrP$^C$ expression at the cell surface (anti-PrP$^C$) as compared to negative control (irrel).

FIG. 6: STI1$_{230-245}$ peptide that represents the binding site at the PrP$^C$ molecule is unable to promote proliferation in A172 glioblastoma cell line. Cells were cultured in serum-free media and subjected to STI1$_{230-245}$ (ELGNDAYKKKD-FDKAL) or STI1/Hop$_{61-76}$ (GCKTVDLKPDWGKGYS) peptide treatment at the indicated concentration for 24 hr. Proliferation was determined by quantitative measurement of [$^3$H]-thymidine incorporation (6.7 uCi/ml, 6-hour pulse). The results are respectively normalized to the rate of proliferation (100%) in serum-free media. (CTR); n=4. Values are means±standard error.

FIG. 7A: Treatment of A172 cells with STI1$_{230-245}$ peptide abrogates cell proliferation mediated by STI1. A172 human glioblastoma cells were plated at 1×10$^4$ confluence on glass cover slips of 12 mm. After overnight adherence, cells were starved on serum-free media for 30 hours. Cells were subjected to distinct treatments (see picture), for 18 hours, and a BrdU pulse of 32 μM was performed on the last 30 minutes of treatment. Immunofluorescence and cell imaging were done in order to permit absolute cell counting. Values represent percentage of BrdU positive cell nuclei from total number of cell nuclei (DAPI staining) on at least four different images of each condition: FCS (fetal calf serum), STI1 (170 nM) and/or STI1$_{230-245}$ peptide (170 nM) or STI1/Hop$_{61-76}$ (irrelevant N-terminus STI1/Hop peptide, 170 nM). *Statistically significant from control (without treatment), p<0.05. Values Bars shown as mean values±SEM.

Figure 7B:
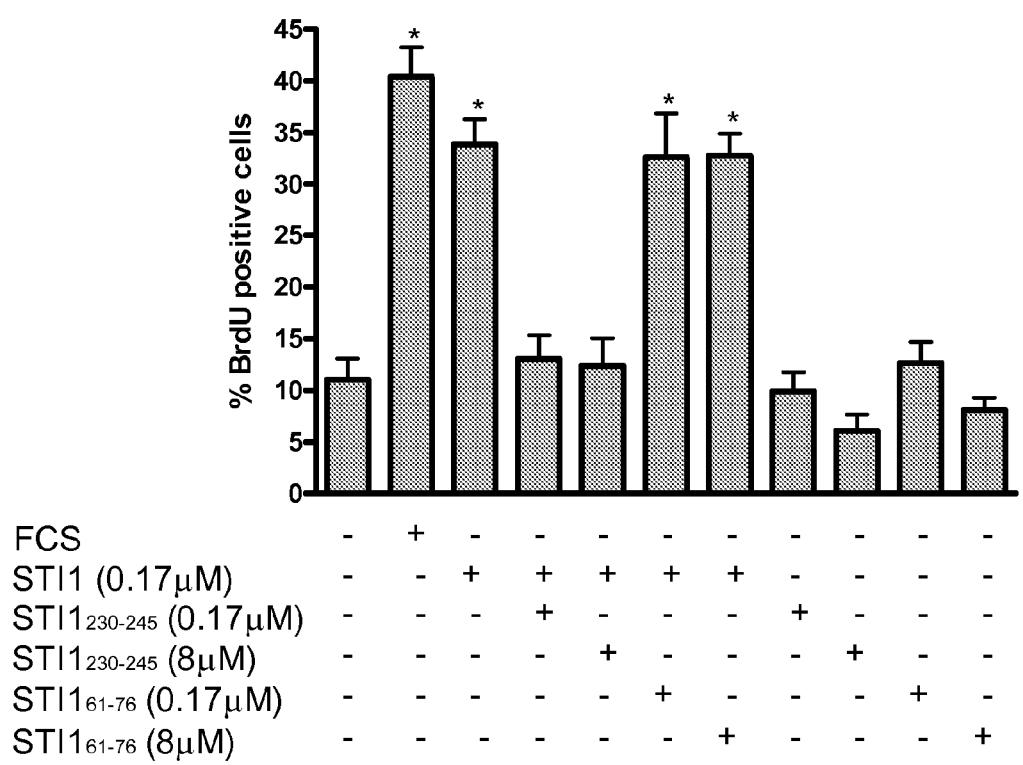

FIG. 7B: Treatment of U87MG cells with STI1$_{230-245}$ peptide abrogates cell proliferation mediated by STI1. U87MG human glioblastoma cells were plated at 1.5×10$^4$ confluence on glass cover slips of 12 mm. After overnight adherence, cells were starved on serum-free media for 48 hours. Cells were subjected to distinct treatments (see picture) for 24 hours, and a BrdU pulse of 32 μM was performed on the last 2 hours of treatment. Immunofluorescence and cell imaging were done in order to permit absolute cell counting. Values represent percentage of BrdU positive cell nuclei from total number of cell nuclei. FCS (fetal calf serum), STI1/Hop (0.17 μM or 8 μM) and/or STI1$_{230-245}$ (0.17 μM or 8 μM) and/or STI1/Hop$_{61-76}$ (irrelevant N-terminus STI1/Hop peptide, 0.17 μM or 8 μM). *Statistically significant from control (without treatment), p<0.001. Bars shown as mean±SEM.

FIG. 8: Hop$_{230-245}$ peptide inhibits the U87MG cell proliferation mediated by STI1. U87MG human glioblastoma cells were plated at 1.5×10$^4$ confluence on glass cover slips of 12 mm. After overnight adherence, cells were starved on serum-free media for 48 hours. Cells were subjected to distinct treatments (see picture) for 24 hours, and a BrdU pulse of 32 μM was performed on the last 2 hours of treatment. Immunofluorescence and cell imaging were done in order to permit absolute cell counting. Values represent percentage of BrdU positive cell nuclei from total number of cell nuclei. STI1 (0.17 μM) and/or Hop$_{230-245}$ (0.17 μM or 8 μM) and/or STI1/Hop$_{61-76}$ (irrelevant STI1/Hop$_{61-76}$, 0.17 μM or 8 μM). *Statistically significant from control (without treatment), p<0.01. Bars shown as mean±SEM.

FIG. 9: Treatment of U87MG cells with TAT-STI1$_{230-245}$ and TAT-Hop$_{230-245}$ peptides inhibits cell proliferation mediated by STI1. U87MG human glioblastoma cells were plated at 1.5×10$^4$ confluence on glass cover slips of 12 mm. After overnight adherence, cells were starved on serum-free media for 48 hours. Cells were subjected to distinct treatments (see picture) for 24 hours, and a BrdU pulse of 32 μM was performed on the last 2 hours of treatment. Immunofluorescence and cell imaging were done in order to permit absolute cell counting. STI1 (0.17 μM) and/or TAT-STI1$_{230-245}$ (0.17 μM) and/or TAT-Hop$_{230-245}$ (0.17 μM). Values represent percentage of BrdU positive cell nuclei from total number of cell nuclei. *Statistically significant from control (without treatment), p<0.01. Dunnets test. Bars shown as mean±SEM.

FIG. 10: Dansyl TAT-STI1$_{230-145}$ peptide effectively labeled U87MG cells. Images exhibit fluorescence microscope imaging of U87MG cells that received a 2-hour treatment of Dansyl TAT-STI1$_{230-245}$ (left panel) and Dansyl TAT-STI1$_{422-437}$ irrelevant (right panel) peptides. Insets show negative controls.

Figure 11:
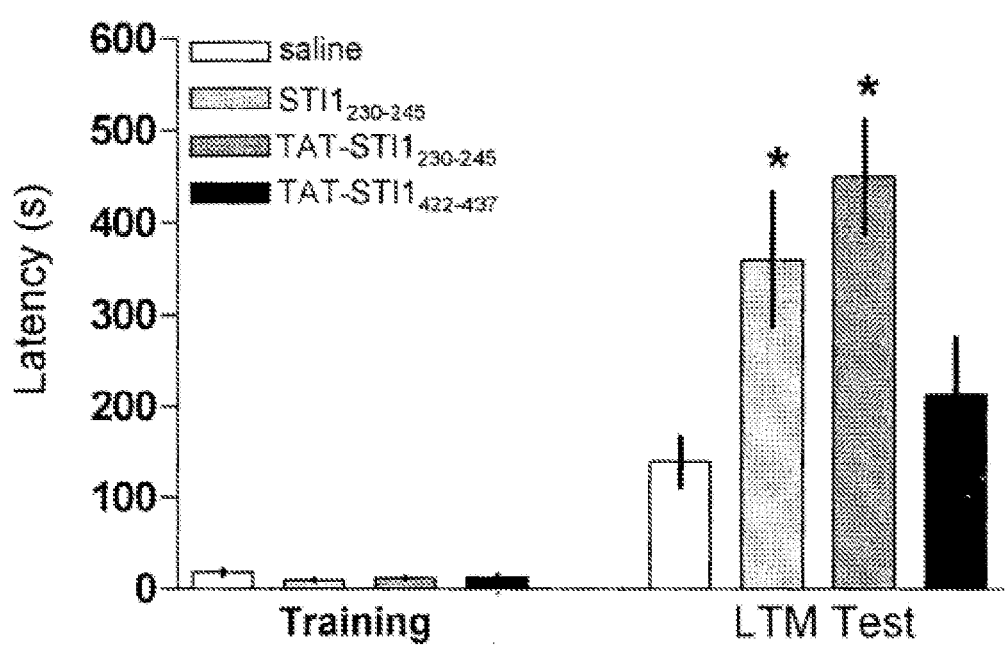
FIG. 11 is a graphic depiction of the results of experiments designed to test the effect of STI1$_{230-245}$, Hop$_{230-245}$ and their TAT-associated forms on memory formation and to test the efficacy of the peptides as neuroprotective agents.

FIG. 11: STI1$_{230-245}$ peptide and TAT-STI1$_{230-245}$ peptides are capable of increasing long-term memory. The latency to step down before treated rats was recorded (Training) and immediately after training animals received a bilateral hippocampal infusion of saline, STI1$_{230-245}$ peptide, TAT-STI1$_{230-245}$ or TAT-STI1$_{61-76}$ irrelevant peptide at the concentration of 15 ng/μl in a total volume of 0.5 μl/side. The latency to step down was tested again 24 hours later (LTM test) and measures Long-term memory (LTM). Data are shown as mean±SE of step-down latencies (n=12 rats in each group). *p<0.05 vs control.

Figure 12:
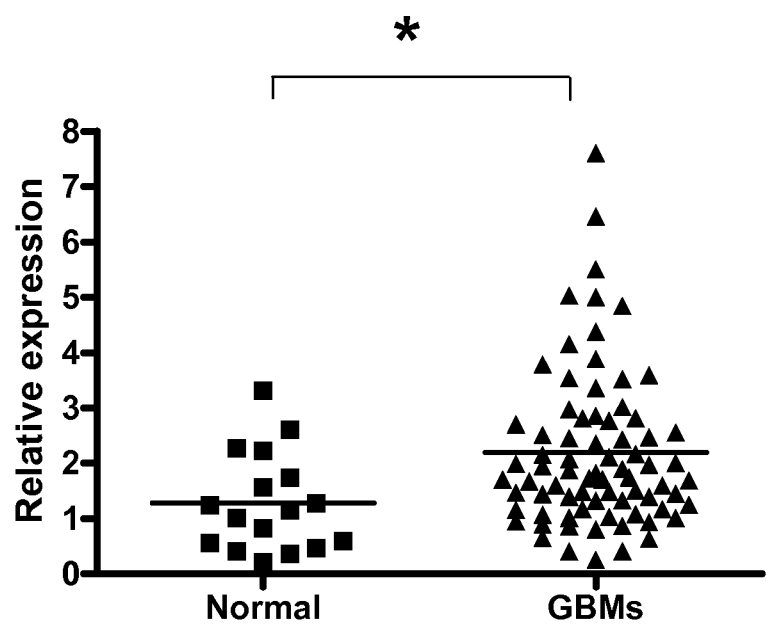
FIG. 12 is a graphic depiction of the results of monitoring Hop gene expression in various glioblastoma samples and normal brain tissue.

FIG. 12: Hop expression in glioblastomas and normal tissue. The mRNA was extracted from normal brain and glioblastomas tissues and RT-PCR was performed to produce cDNA. Total cDNA obtained from 17 normal brain tissues and 76 glioblastoma samples were evaluated for Hop relative expression in both tissues using Real time-PCR. *Statistically significant from normal tissues, p<0.05. Bars represent mean values.

We claim:

1. A method for the treatment of cancer, which comprises administering to a patient in need thereof an effective amount of a peptide that inhibits the interaction between PrP$^C$ and Hop, thus inhibiting the Hop-induced proliferation of the cancer cells, wherein the peptide is selected from the group consisting of ELGNDAYKKKDFDKAL (SEQ ID NO: 1), ELGNDAYKKKDFDTAL (SEQ ID NO: 2), YGRKKRRQRRRELGNDAYKKKDFDTAL (SEQ ID NO: 10), YGRKKRRQRRRELGNDAYKKKDFDKAL (SEQ ID NO: 9), TFFYGGCRGKRNNFKTEEYELGN-DAYKKKDFDTAL (SEQ ID NO: 12), and TFFYG-GCRGKRNNFKTEEYELGNDAYKKKDFDKAL (SEQ ID NO: 13).

2. The method according to claim 1, wherein the cancer is selected from glioma, glioblastoma, medulloblastoma, astrocytoma, colon cancer, colorectal cancer and gastric cancer.

3. The method according to claim 2, wherein the cancer is a glioma.

4. A method for alleviating or eliminating the side effects of drug therapy and radiotherapy used in treating patients with brain cancers, which comprises administering to such a patient an effective amount of a peptide that inhibits the interaction between PrP$^C$ and Hop, wherein the peptide is selected from the group consisting of ELGNDAYKKKDFD-KAL (SEQ ID NO: 1), ELGNDAYKKKDFDTAL (SEQ ID NO: 2), YGRKKRRQRRRELGNDAYKKKDFDTAL (SEQ ID NO: 10), YGRKKRRQRRRELGNDAYKKKDFDKAL (SEQ ID NO: 9), TFFYGGCRGKRNNFKTEEYELGN-DAYKKKDFDTAL (SEQ ID NO: 12), and TFFYG-GCRGKRNNFKTEEYELGNDAYKKKDFDKAL (SEQ ID NO: 13).

5. The method according to claim 4, wherein the cancer is selected from glioma, glioblastoma, medulloblastoma and astrocytoma.

6. The method according to claim 5, wherein the cancer is a glioma.

* * * * *